United States Patent
Buller et al.

(10) Patent No.: US 9,790,475 B2
(45) Date of Patent: Oct. 17, 2017

(54) HUMAN SERUM ALBUMIN BINDING COMPOUNDS AND FUSION PROTEINS THEREOF

(71) Applicant: COVAGEN AG, Zug (CH)

(72) Inventors: Fabian Buller, Zürich (CH); Ulrich Wüllner, Oberengstringen (CH); Irene Zbinden, Turbenthal (CH); Isabella Attinger-Toller, Zürich (CH); Ulrike Von Der Bey, Orsingen-Nenzingen (DE); Susann König-Friedrich, Gottmadingen (DE); Julian Bertschinger, Ottenbach (CH); Dragan Grabulovski, Zürich (CH); Patricia Henne, Spreitenbach (CH)

(73) Assignee: Covagen AG, Zug (CH)

( * ) Notice: Subject to any disclaimer, the term of this patent is extended or adjusted under 35 U.S.C. 154(b) by 0 days.

(21) Appl. No.: 14/758,339

(22) PCT Filed: Dec. 18, 2013

(86) PCT No.: PCT/EP2013/077227
§ 371 (c)(1),
(2) Date: Jun. 29, 2015

(87) PCT Pub. No.: WO2014/106583
PCT Pub. Date: Jul. 10, 2014

(65) Prior Publication Data
US 2016/0076011 A1  Mar. 17, 2016

(30) Foreign Application Priority Data
Jan. 3, 2013 (EP) .................... 13150171

(51) Int. Cl.
| | | |
|---|---|---|
| *C07K 14/00* | (2006.01) | |
| *C12N 9/12* | (2006.01) | |
| *C07K 14/765* | (2006.01) | |
| *C07K 14/47* | (2006.01) | |
| *C07K 16/18* | (2006.01) | |

(52) U.S. Cl.
CPC ............ *C12N 9/12* (2013.01); *C07K 14/47* (2013.01); *C07K 14/765* (2013.01); *C07K 16/18* (2013.01); *C07K 2317/31* (2013.01); *C07K 2319/31* (2013.01); *C12Y 207/10002* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 6,080,560 A | 6/2000 | Russell et al. | |
| 9,085,760 B2 * | 7/2015 | Brack | C07K 14/4703 |
| 2010/0119446 A1 * | 5/2010 | Grabulovski | C12N 9/1205 424/1.69 |
| 2015/0047065 A1 * | 2/2015 | Brack | A61K 39/39591 800/18 |

FOREIGN PATENT DOCUMENTS

| | | |
|---|---|---|
| EP | 0239400 B1 | 8/1994 |
| EP | 1892248 A1 | 2/2008 |
| EP | 2524927 A1 | 11/2012 |
| EP | 2054432 B1 | 7/2015 |

(Continued)

OTHER PUBLICATIONS

Dennis MS, et al., "Albumin Binding as a General Strategy for Improving the Pharmacokinetics of Proteins", *Journal of Biological Chemistry*, 277(38), p. 35035-35043 (2002).
Jonsson A. et al.,"Engineering of a femtomolar affinity binding protein to human serum albumin", *Protein Engineering, Design & Selection*, 21(8), p. 515-527 (2008).
Holt L. J. et al., "Anti-serum albumindomain antibodies for extending the half-lives of short lived drugs", *Protein Engineering Design & Selection*, 21 (5), p. 283-288 (2008).
Walker A., et al., "Anti-serum albumin domain antibodies in the development of highly potent, efficacious and long-acting interferon", *Protein Engineering, Design & Selection* 23(4), p. 271-278 (2010).

(Continued)

*Primary Examiner* — Anand Desai
(74) *Attorney, Agent, or Firm* — Brian C. Carey

(57) ABSTRACT

The present invention relates to a polypeptide binding to human serum albumin and comprising or consisting of an amino acid sequence selected from the group consisting of: (a) GVTLFVALYDY($X^1$)($X^2$)($X^3$)($X^4$)($X^5$) ($X^6$)D($X^7$)SF-HKGEKFQIL($X^8$)($X^9$)($X^{10}$)($X^{11}$)($X^{12}$)G($X^{13}$)($X^{14}$)W($X^{15}$) ($X^{16}$)RSLTTG($X^{17}$)($X^{18}$)G($X^{19}$)IPSNYVAPVDSIQ (SEQ ID NO: 1), wherein ($X^1$) is A, V, I, L, M, G, P, S, T, N, Q, C, R, H, K, D or E; ($X^2$) is R, H, K, A, V, I, L, M, G, P, S, T, N, Q or C; ($X^3$) is R, H, K, S, T, N, Q, C, F, Y, W, A, V, I, L, M, G or P; ($X^4$) is S, T, N, Q, C, A, V, I, L, M, G, P, R, H, K, F, Y, W, D or E; ($X^5$) is S, T, N, Q, C, D, E, F, Y, W, A, V, I, L, M, G, P, R, H or K; ($X^6$) is F, Y, W, A, V, I, L, M, G, P, R, H, K, S, T, N, Q or C; ($X^7$) is A, V, I, L, M, G, P, R, H or K; ($X^8$) is S, T, N, Q, C, D or E; ($X^9$) is S, T, N, Q, C, D, E, A, V, I, L, M, G, P, F, Y or W; ($X^{10}$) is A, V, I, L, M, G or P; ($X^{11}$) is F, Y, W, R, H or K; ($X^{12}$) is S, T, N, Q, C, F, Y or W; ($X^{13}$) is F, Y, W, R, H, K, S, T, N, Q, C, D, E, A, V, I, L, M, G or P; ($X^{14}$) is F, Y, W, A, V, I, L, M, G or P; ($X^{15}$) is D, E, A, V, I, L, M, G or P; ($X^{16}$) is A, V, I, L, M, G or P; ($X^{17}$) is D, E, A, V, I, L, M, G, P, R, H or K; ($X^{18}$) is S, T, N, Q, C, A, V, I, L, M, G or P; ($X^{19}$) is F, Y, W, S, T, N, Q or C; and (b) an amino acid sequence which is at least 90% identical to the amino acid sequence of (a), wherein the identity determination excludes amino acid positions ($X^1$) to ($X^{19}$).

8 Claims, 9 Drawing Sheets

(56) References Cited

FOREIGN PATENT DOCUMENTS

| WO | WO 90/07861 A1 | 7/1990 |
| WO | WO 91/01743 A1 | 1/1991 |
| WO | WO 01/45746 A2 | 6/2001 |
| WO | WO 02/076489 A2 | 10/2002 |
| WO | WO 2004/041865 A2 | 5/2004 |

OTHER PUBLICATIONS

Skerra A., "Engineered protein scaffolds for molecular recognition", *Journal of Molecular Recognition*, 13, p. 167-187 (2000).

Gebauer M. et al., "Engineered protein scaffolds as next-generation antibody therapeutics", *Current Opinion in Chemical Biology*, 13, p. 245-255 (2009).

Bertschinger J. et al., "Selection of single domain binding proteins by covalent DNS display", *Protein, Engineering, Design & Selection*, 20(2), p. 57-68 (2007).

Altschul, S. et al., "Gapped BLAST and PSI-BLAST: a new generation of protein database search programs", *Nucleic Acids Res.* 25, p. 3389-3402 (1997).

Sangastino et al., "Safety and pharmacokinetics of a novel recombinant fusion protein linking coagulation factor IX with albumin (rIX-RP) in hemophilia B patients", *Blood*, 120(12), p. 2405-2411 (2012).

Musacchio et al., "Structure and Function of the SH3 Domain", *Prog. Biophys. Mol. Biol.* 61, p. 283-297 (1994).

Musacchio et al.,"How SH3 Domains Recognize Proline", *Advances in Protein Chemistry* 61, p. 211-268 (2003).

Ren et al., "Identification of a Ten-Amino Acid Proline-Rich SH3 Binding Site", *Science* 259, p. 1157-1161 (1993).

Karkkainen et al., "Identification of preferred protein interactions by phage-display of the human Src homology-3 proteome", *EMBO Report* 7(2), p. 186-191 (2006).

Koyama et al., Structure of the PI3K SH3 Domain and Analysis of the SH3 Family, *Cell* 72(6), p. 945-952 (1993).

Larson et al., "The identification of conserved interactions within the SH3 domain by alignment of sequences and structures", *Protein Science* 9, p. 2170-2180 (2000).

Erpel et al., "Mutational analysis of the Src SH3 domain: the same residues of the ligand binding surface are important for intra- and intermolecular interactions", *The EMBO Journal*, 14(4), p. 963-75 (1995).

Grabulovski et al., "A Novel, Non-immunogenic Fyn SH3-derived Binding Protein with Tumor Vascular Targeting Properties", *Journal of Biological Chemistry*, 282, p. 3196-3204 (2007).

Alberts et al., "Fusion Proteins Can Be Used to Analyze Protein Function and to Track Proteins in Living Cells" *Molecular Biology of the Cell*, 4th ed Garland Science, p. 518-519 (2002).

Kawakami et al. "Isolation and oncogenic potential of a novel human src-like gene", *Molecular and Cellular Biology*, 6 (12) 4195-4201(1986).

Semba K. et al. "Yes-related protooncogene, syn, belongs to the protein-tyrosine kinase family", *Proc Natl Acad Sci USA* 83 (15) pp. 5459-5463 (1986).

Altshuler et al. "Generation of Recombinant Antibodies and Means for Increasing Their Affinity", *Biochemistry* (Moscow) 75 (13), pp. 1584-1605 (2010).

Holliger et al., "Engineered antibody fragments and the rise of single domains", *Nature Biotechnology*, 23 (9), pp. 1126-1136 (2005).

Kohelr & Milstein, "Continuous cultures iof fused cells secreting antibody of predefined specificity", *Nature* 256, pp. 495-497 (1975).

Kozbor, "The production of monoclonal antibodies from human lymphocytes", *Immunology Today*, 4, p. 72 (1983).

Li et al., "Human antibodies for immunotherapy development generated via a human B cell hybridoma technology", *PNAS*, 103 (10) pp. 3557-3562 (2006).

Cole et al., "The EBV-Hybridoma Technique and its Application to Human Lung Cancer", *Monoclonal Antibodies and Cancer Therapy*, Alan R. Liss Inc. p. 77-96 (1985).

Strohl W., "Optimization of Fc-mediated effector functions of monoclonal antibodies", *Current Opinion Biotechnology*, 20, p. 685-691 (2009).

Baeuerle PA. et al., "Bispecific antibodies for polyclona T-cell engagement", *Current Opinion Molecular Therapy* 5(4), p. 413-419 (2003).

Wolf E., et al., "BiTEs bispecific antibody constructs with unique anti-tumor activity", *Drug Discovery Today*, 10(18), p. 1237-1244 (2005).

Bauerle PA et al., "Bispecific T-cell Engaging Antibodies for Cancer Therapy", *Cancer Research*, 69 (12), p. 4941-4944 (2009).

Friedrich M. et al., "Regression of Human Prostate Cancer Xenografts in Mice by AMG 212/BAY2010112, a Novel PSMA/CD3-Bispecific BiTE Antibody Cross-Reactive with Non-Human Primate Antigens", *Molecular Cancer Therapy*, 11, p. 2664-2674 (2012).

Braasch et al., "Locked nucleic acid (LNA): fine-tuning the recognition of DNA and RNA", *Chemistry & Biology*, 8, p. 1-7 (2001).

Owens et al., "Identification of two short internal ribosome entry sites selected from libraries of random oligonucleotides", *Proc Natl Acad Sci, USA* 98(4), p. 1471-1476 (2001).

Ghahroudi et al., "Selection and identification of single domain antibody fragments from camel heavy-chain antibodies", *FEBS Letters* 414, p. 521-526 (1997).

Schlatter et al., "Generation, characterization and structural data of chymase binding proteins based on the human Fyn kinase SH3 domain", *mABS*, 4(4), p. 497-50 (2012), Jan. 8, 2017.

Viti, F. et al., "Design and Use of Phage Display Libraries for the Selection of Antibodies and Enzymes", *Methods in Enzymology* 326, p. 480-505 (2000).

Dreier et al., "Extremely Potent, Rapid and Costimuation-Independent Cytotoxic T-Cell Response Against Lymphoma Cells Catalyzed by a Single-Chain Bispecific Antibody", *Int. J. Cancer*, 100, p. 690-697 (2002).

Grabulovski, Dragan, "The SH3 of fyn kinase as a scaffold for the generation of a new binding proteins" ETH Dissertation NR17216 http://dx/doi/org/10.3929/ethz-a-005407897 (2007).

Lee et al., A single amino acid in the SH3 domain of Hck determines its high affinity and specificity in binding to HIV-1 Nef protein:, *The Embo Journal*, vol. 14, No. 20, p. 5006-5015, XP002236097 (1995).

\* cited by examiner

Figure 8:

CLUSTAL W (1.83) multiple sequence alignment
C1 (SEQ ID NO: 4)
GVTLFVALYDYHAHLGYDLSFHKGEKFQILQDLWTGDWWEARSLTTGETGYIPSNYVAPVDSIQ 17H (SEQ ID NO: 5)
GVTLFVALYDYQSRHGFDLSFHKGEKFQILQNLWTGDWWEARSLTTGETGYIPSNYVAPVDSIQ AB15F (SEQ ID NO: 6)
GVTLFVALYDYVSNTGFDLSFHKGEKFQILQNLWTGDWWEARSLTTGETGYIPSNYVAPVDSIQ AB19C4 (SEQ ID NO: 7)
GVTLFVALYDYTASYGYDLSFHKGEKFQILDDIWTGDWWEARSLTTGETGYIPSNYVAPVDSIQ SAM5H5 (SEQ ID NO: 8)
GVTLFVALYDYLRRNSPDLSFHKGEKFQILQNLWTGDWWEARSLTTGETGYIPSNYVAPVDSIQ SAM7G4 (SEQ ID NO: 9)
GVTLFVALYDYHAHLGYDLSFHKGEKFQILQDLWTGALWRARSLTTGRMGSIPSNYVAPVDSIQ SAM23C5 (SEQ ID NO: 10)
GVTLFVALYDYQSRHGFDLSFHKGEKFQILQNLWTGEWWEARSLTTGETGYIPSNYVAPVDSIQ SAM22A2 (SEQ ID NO: 11)
GVTLFVALYDYQSRHGFDLSFHKGEKFQILQNLWTGSWWEARSLTTGETGYIPSNYVAPVDSIQ SAM23F4 (SEQ ID NO: 12)
GVTLFVALYDYQSRHGFDLSFHKGEKFQILQNLWTGKWWEARSLTTGETGYIPSNYVAPVDSIQ SAM11C1 (SEQ ID NO: 13)
GVTLFVALYDYEKQHAWDLSFHKGEKFQILQNLWTGDWWEARSLTTGETGYIPSNYVAPVDSIQ SAM11E6 (SEQ ID NO: 14)
GVTLFVALYDYRSSYEWDLSFHKGEKFQILQNLWTGDWWEARSLTTGETGYIPSNYVAPVDSIQ SAM23C9 (SEQ ID NO: 15)
GVTLFVALYDYQSRHGFDLSFHKGEKFQILQNLWTGNWWEARSLTTGETGYIPSNYVAPVDSIQ SAM19G2 (SEQ ID NO: 16)
GVTLFVALYDYHAHLGYDLSFHKGEKFQILQNLWTGDWWEARSLTTGETGYIPSNYVAPVDSIQ SAM19F9 (SEQ ID NO: 17)
GVTLFVALYDYGNFRWRDLSFHKGEKFQILQNLWTGDWWEARSLTTGETGYIPSNYVAPVDSIQ SAM20F11 (SEQ ID NO: 18)
GVTLFVALYDYQSRHGFDLSFHKGEKFQILQNLWTGWGWVARSLTTGLSGYIPSNYVAPVDSIQ SAM21D10 (SEQ ID NO: 19)
GVTLFVALYDYTSMRGYDLSFHKGEKFQILQDLWTGDWWEARSLTTGETGYIPSNYVAPVDSIQ SAM21E1 (SEQ ID NO: 20)
GVTLFVALYDYQSKHGYDLSFHKGEKFQILQDLWTGDWWEARSLTTGETGYIPSNYVAPVDSIQ SAM21G3 (SEQ ID NO: 21)
GVTLFVALYDYLMKTLADLSFHKGEKFQILQDLWTGDWWEARSLTTGETGYIPSNYVAPVDSIQ SAM22B3 (SEQ ID NO: 22)
GVTLFVALYDYTLRQWKDLSFHKGEKFQILQNLWTGDWWEARSLTTGETGYIPSNYVAPVDSIQ

Figure 8 - continued:

SAM22B8 (SEQ ID NO: 23)
GVTLFVALYDYERQHGFDLSFHKGEKFQILQNLWTGDWWEARSLTTGETGYIPSNYVAPVDSIQ

SAM22B7 (SEQ ID NO: 24)
GVTLFVALYDYESRHGYDLSFHKGEKFQILQNLWTGDWWEARSLTTGETGYIPSNYVAPVDSIQ

SAM22E3 (SEQ ID NO: 25)
GVTLFVALYDYQSKQGFDLSFHKGEKFQILQNLWTGDWWEARSLTTGETGYIPSNYVAPVDSIQ

SAM28B1 (SEQ ID NO: 26)
GVTLFVALYDYLLQWRQDLSFHKGEKFQILQDLWTGDWWEARSLTTGETGYIPSNYVAPVDSIQ

SAM28B9 (SEQ ID NO: 27)
GVTLFVALYDYTSSHGFDLSFHKGEKFQILQDLWTGDWWEVRSLTTGETGYIPSNYVAPVDSIQ

SAM30H2 (SEQ ID NO: 28)
GVTLFVALYDYEAHLGYDLSFHKGEKFQILQNLWTGDWWEARSLTTGETGYIPSNYVAPVDSIQ

SAM30D6 (SEQ ID NO: 29)
GVTLFVALYDYTAVHGYDLSFHKGEKFQILQNLWTGDWWEARSLTTGETGYIPSNYVAPVDSIQ

SAM30B8 (SEQ ID NO: 30)
GVTLFVALYDYLTKQLPDRSFHKGEKFQILQNLWTGDWWEARSLTTGETGYIPSNYVAPVDSIQ

SAM30B12 (SEQ ID NO: 31)
GVTLFVALYDYMSQMGYDLSFHKGEKFQILQNLWTGDWWEARSLTTGETGYIPSNYVAPVDSIQ

SAM31H9 (SEQ ID NO: 32)
GVTLFVALYDYQASHGYDLSFHKGEKFQILQNLWTGDWWEARSLTTGETGYIPSNYVAPVDSIQ

AB8F11 (SEQ ID NO: 33)
GVTLFVALYDYTARTGYDLSFHKGEKFQILDAVRFGDWWEARSLTTGETGYIPSNYVAPVDSIQ

AB18G9 (SEQ ID NO: 34)
GVTLFVALYDYQSREKFDLSFHKGEKFQILDQLRFGDWWEARSLTTGETGYIPSNYVAPVDSIQ

SAM14D1 (SEQ ID NO: 35)
GVTLFVALYDYQSRHGFDLSFHKGEKFQILDNLRFGDWWEARSLTTGETGYIPSNYVAPVDSIQ

SAM14C3 (SEQ ID NO: 36)
GVTLFVALYDYHAHLGYDLSFHKGEKFQILDDLRFGDWWEARSLTTGETGYIPSNYVAPVDSIQ

SAM17F1 (SEQ ID NO: 37)
GVTLFVALYDYQSRHGFDLSFHKGEKFQILDWLRFGDWWEARSLTTGETGYIPSNYVAPVDSIQ

SAM17B3 (SEQ ID NO: 38)
GVTLFVALYDYQSRHGFDLSFHKGEKFQILDAIRFGDRWEARSLTTGETGYIPSNYVAPVDSIQ

SAM17F3 (SEQ ID NO: 39)
GVTLFVALYDYQSRHGFDLSFHKGEKFQILDMLRFGDWWEARSLTTGETGYIPSNYVAPVDSIQ

SAM17H4 (SEQ ID NO: 40)
GVTLFVALYDYHAHLGYDLSFHKGEKFQILDSLRFGDWWEARSLTTGETGYIPSNYVAPVDSIQ

*********** * ***********: : * * .****** * *************

HUMAN SERUM ALBUMIN BINDING COMPOUNDS AND FUSION PROTEINS THEREOF

The present invention relates to a polypeptide binding to human serum albumin and comprising or consisting of an amino acid sequence selected from the group consisting of: (a) GVTLFVALYDY($X^1$)($X^2$)($X^3$)($X^4$)($X^5$)($X^6$)D($X^7$)SFH-KGEKFQIL($X^8$)($X^9$)($X^{10}$)($X^{11}$)($X^{12}$)G($X^{13}$)($X^{14}$)W($X^{15}$)($X^{16}$)RSLTTG($X^{17}$)($X^{18}$)G($X^{19}$)IPSNYVAPVDSIQ (SEQ ID NO: 1), wherein ($X^1$) is A, V, I, L, M, G, P, S, T, N, Q, C, R, H, K, D or E; ($X^2$) is R, H, K, A, V, I, L, M, G, P, S, T, N, Q or C; ($X^3$) is R, H, K, S, T, N, Q, C, F, Y, W, A, V, I, L, M, G or P; ($X^4$) is S, T, N, Q, C, A, V, I, L, M, G, P, R, H, K, F, Y, W, D or E; ($X^5$) is S, T, N, Q, C, D, E, F, Y, W, A, V, I, L, M, G, P, R, H or K; ($X^6$) is F, Y, W, A, V, I, L, M, G, P, R, H, K, S, T, N, Q or C; ($X^7$) is A, V, I, L, M, G, P, R, H or K; ($X^8$) is S, T, N, Q, C, D or E; ($X^9$) is S, T, N, Q, C, D, E, A, V, I, L, M, G, P, F, Y or W; ($X^{10}$) is A, V, I, L, M, G or P; ($X^{11}$) is F, Y, W, R, H or K; ($X^{12}$) is S, T, N, Q, C, F, Y or W; ($X^{13}$) is F, Y, W, R, H, K, S, T, N, Q, C, D, E, A, V, I, L, M, G or P; ($X^{14}$) is F, Y, W, A, V, I, L, M, G or P; ($X^{15}$) is D, E, A, V, I, L, M, G or P; ($X^{16}$) is A, V, I, L, M, G or P; ($X^{17}$) is D, E, A, V, I, L, M, G, P, R, H or K; ($X^{18}$) is S, T, N, Q, C, A, V, I, L, M, G or P; ($X^{19}$) is F, Y, W, S, T, N, Q or C; and (b) an amino acid sequence which is at least 90% identical to the amino acid sequence of (a), wherein the identity determination excludes amino acid positions ($X^1$) to ($X^{19}$).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Many therapeutics and diagnostics, in particular biologicals (i.e. peptide or polypeptide drugs, polynucleotides, etc.) suffer from inadequate serum half-lives in vivo. This necessitates the administration of such therapeutics at constant infusions, or high frequencies and/or high doses, or the use of sustained release formulations, in order to maintain the serum levels necessary for therapeutic effects. Frequent systemic administration of drugs is associated with considerable negative side effects. For example, frequent, e.g. daily, systemic injections represent a considerable discomfort to the subject, and pose a high risk of administration related infections, and may require hospitalization or frequent visits to the hospital, in particular when the therapeutic is to be administered intravenously. Moreover, in long term treatments daily intravenous injections can also lead to considerable side effects of tissue scarring and vascular pathologies caused by the repeated puncturing of vessels. Similar problems are known for all frequent systemic administrations of therapeutics, like, for example, the administration of insulin to diabetics, or interferon drugs in patients suffering from multiple sclerosis. All these factors lead to a decreased patient compliance and increased costs for the health system.

One avenue of prolonging the in vivo half-life of otherwise short-lived protein therapeutics and molecules represents the fusion of these compounds to polypeptides that bind to human serum albumin. Polypeptides that are capable of binding to serum albumin and uses thereof in polypeptide constructs in order to increase the half-life of therapeutically relevant proteins and polypeptides are known in the art (Dennis M S et al (2002) *J Biol Chem,* 277(38) p. 35035-35043; Jonsson A. et al., (2008) *Protein Eng Des Sel,* 21(8), p. 515-527). Moreover, WO 91/01743, WO 01/45746 and WO 02/076489 describe peptide moieties binding to serum albumin that can be fused to therapeutic proteins and other therapeutic compounds and entities in order to increase the half-life thereof. However, these peptide moieties are of bacterial or synthetic origin, which is less preferred for use in therapeutics. Other binding domains to albumin comprise Nanobodies® (derived from camelids) (WO 04/041865) and single domain antibodies (derived from human antibodies) (Holt L. J. et al. (2008) *Protein Eng Des Sel,* 21, p. 283-288 and Walker, A. et al. (2010) *Protein Eng Des Sel* 23, p. 271-278).

One avenue of obtaining high affinity and specific binding proteins to serum albumin with desired pharmacokinetic and pharmacodynamic properties, represents the use of antibody and alternative binding technologies (the latter termed "scaffolds"). These non-immunoglobulin-derived binding reagents are known in the art and are collectively designated "scaffolds" (Skerra A. (2000) J. Mol. Recognit. 13, 167-187). More than 50 different protein scaffolds have been proposed over the past 10 to 15 years, the most advanced approaches in this field being (as summarized in Gebauer M and Skerra A. (2009) Curr Opinion in Chemical Biology 13:245-255): Affibodies® (based on the Z-domain of staphylococcal protein A), Kunitz type domains, adnectins (based on the 10th domain of human fibronectin), Anticalins® (derived from lipocalins), DARPins (derived from ankyrin repeat proteins), avimers (based on multimerized LDLR-A), and Fynomers® (Bertschinger J. et al., (2007), Protein Eng Des Sel, 20(2), p. 57-68 and EP 2054432), which are derived from the human Fyn SH3 domain.

As is evident from the above, there is an ongoing need for further means to prolong the in vivo half-life of pharmaceutically and/or diagnostically active proteins or peptides. This need is addressed by the present invention.

Accordingly the present invention relates in a first embodiment to a polypeptide binding to human serum albumin and comprising or consisting of an amino acid sequence selected from the group consisting of: (a) GVTLFVALYDY($X^1$)($X^2$)($X^3$)($X^4$)($X^5$)($X^6$)D($X^7$)SFHK-GEKFQIL($X^8$)($X^9$)($X^{10}$)($X^{11}$)($X^{12}$)G($X^{13}$)($X^{14}$)W ($X^{15}$)($X^{16}$)RSLTTG($X^{17}$)($X^{18}$)G($X^{19}$)IPSNYVAPVDSIQ (SEQ ID NO: 1), wherein ($X^1$) is A, V, I, L, M, G, P, S, T, N, Q, C, R, H, K, D or E; ($X^2$) is R, H, K, A, V, I, L, M, G, P, S, T, N, Q or C; ($X^3$) is R, H, K, S, T, N, Q, C, F, Y, W, A, V, I, L, M, G or P; ($X^4$) is S, T, N, Q, C, A, V, I, L, M, G, P, R, H, K, F, Y, W, D or E; ($X^5$) is S, T, N, Q, C, D, E, F, Y, W, A, V, I, L, M, G, P, R, H or K; ($X^6$) is F, Y, W, A, V, I, L, M, G, P, R, H, K, S, T, N, Q or C; ($X^7$) is A, V, I, L, M, G, P, R, H or K; ($X^8$) is S, T, N, Q, C, D or E; ($X^9$) is S, T, N, Q, C, D, E, A, V, I, L, M, G, P, F, Y or W; ($X^{10}$) is A, V, I, L, M, G or P; ($X^{11}$) is F, Y, W, R, H or K; ($X^{12}$) is S, T, N, Q, C, F, Y or W; ($X^{13}$) is F, Y, W, R, H, K, S, T, N, Q, C, D, E, A, V, I, L, M, G or P; ($X^{14}$) is F, Y, W, A, V, I, L, M, G or P; ($X^{15}$) is D, E, A, V, I, L, M, G or P; ($X^{16}$) is A, V, I, L, M, G or P; ($X^{17}$) is D, E, A, V, I, L, M, G, P, R, H or K; ($X^{18}$) is S, T, N, Q, C, A, V, I, L, M, G or P; ($X^{19}$) is F, Y, W, S, T, N, Q or C; and (b) an amino acid sequence which is at least 90% identical to the amino acid sequence of (a), wherein the identity determination excludes amino acid positions ($X^1$) to ($X^{19}$).

According to a preferred embodiment of the invention the polypeptide comprises or consists of an amino acid sequence selected from the group consisting of: (a) GVTLFVALYDY $(X^1)(X^2)(X^3)(X^4)(X^5)(X^6)D(X^7)$SFHKGEKFQIL$(X^8)(X^9)$ $(X^{10})(X^{11})(X^{12})$G$(X^{13})(X^{14})$W$(X^{15})$ $(X^{16})$RSLTTG$(X^{17})$ $(X^{18})$G$(X^{19})$IPSNYVAPVDSIQ (SEQ ID NO: 2), wherein $(X^1)$ is V, T, L, H, Q, E, R, G or M; $(X^2)$ is S, A, R; K, N, M, L or T; $(X^3)$ is N, S, R, H, Q, F, M, K or V; $(X^4)$ is T, Y, N, L, H, R, Q, W, M or E; $(X^5)$ is G, S, A, E, W, L, R or K; $(X^6)$ is F, Y P, W, R or Q; $(X^7)$ is L or R; $(X^8)$ is Q or D; $(X^9)$ is N, D, A, Q, W, M or S; $(X^{10})$ is L, I or V; $(X^{11})$ is W or R; $(X^{12})$ is T or F; $(X^{13})$ is D, W, N, K, S, E or A; $(X^{14})$ is W or G; $(X^{15})$ is E or V; $(X^{16})$ is A or V; $(X^{17})$ is E, L or R; $(X^{18})$ is T, S or M; $(X^{19})$ is Y or S; and (b) an amino acid sequence which is at least 90% identical to the amino acid sequence of (a), wherein the identity determination excludes amino acid positions $(X^1)$ to $(X^{19})$.

The term "polypeptide" as used herein describes linear molecular chains of amino acids, including single chain proteins or their fragments, containing more than about 50 amino acids. Polypeptides may further form oligomers consisting of at least two identical or different molecules. The corresponding higher order structures of such multimers are, correspondingly, termed homo- or heterodimers, homo- or heterotrimers etc. Homodimers, trimers etc. also fall under the definition of the term "polypeptide". Furthermore, peptidomimetics of such polypeptides where amino acid(s) and/or peptide bond(s) have been replaced by functional analogs are also encompassed by the invention. Such functional analogues include all known amino acids other than the 20 gene-encoded amino acids, such as selenocysteine. The term "polypeptide" also refers to naturally modified polypeptides where the modification is effected e.g. by glycosylation, acetylation, phosphorylation and similar modifications which are well-known in the art.

Also comprised by the present invention are fragments of the polypeptide of the invention which substantially retain binding to a human serum albumin. In this regard it is preferred with increasing preference that the fragments (which contain in any case less than 50 amino acids) comprise at least 30 amino acids, at least 35 amino acids, at least 40 amino acids, or at least 45 amino acids. It is moreover preferred that in the fragment the amino acid positions corresponding to the RT- and n-Src-loop and the amino acids which are adjacent (e.g. 1, 2, 3, 4, 5, or 6 adjacent amino acid positions) to these loops as defined herein below are retained.

The term "binding to a human serum albumin" requires that the polypeptides of the invention have a specific (in vivo and/or in vitro) binding affinity to a human serum albumin, and more preferably to the human serum albumin of SEQ ID NO: 46. With increasing preference such polypeptides have a dissociation constant ($K_D$) to human serum albumin of less than 5000 nM, less than 2500 nM, and less than 1500 nM. Also such polypeptides have with increasing preference a dissociation constant ($K_D$) to any protein other than mammalian serum albumins of greater than 50000 nM, greater than 100000 nM, and greater than 500000 nM.

As is evident from the examples herein below, binding can be detected using well-known experiments in the art, such as enzyme-linked immunosorbent assay (ELISA) or surface plasmon resonance (SPR) experiments. Such assays may preferably be performed as outlined in the examples herein below.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 90% or 95% identity) may be determined, when the (sub)sequences are compared and aligned for maximum correspondence over a window of comparison, or over a designated region as measured using a sequence comparison algorithm as known in the art, or when manually aligned and visually inspected. The sequences which are compared to determine sequence identity may thus differ by substitution(s), addition(s) or deletion(s) of nucleotides or amino acids. This definition also applies to the complement of a test sequence.

The skilled person is also aware of suitable programs to align nucleic acid sequences. The percentage sequence identity of polypeptide sequences can, for example, be determined with programmes as the above explained programmes CLUSTALW, FASTA and BLAST. Preferably the BLAST programme is used, namely the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402).

With regard to the sequence identity as recited in item (b) herein, it is preferred with increasing preference that the sequence identity is at least 95% or at least 98%.

The phrase "the identity determination excludes amino acid positions $(X^1)$ to $(X^{19})$" as used herein specifies that the calculation of the sequence identity with regard to SEQ ID NOs 1 and 2 (or SEQ ID NOs 41, 42 and 49) does not take into a account amino acid positions $(X^1)$ to $(X^{19})$ but is confined to the remainder of the amino acids positions of SEQ ID NO: 1 or 2 (or SEQ ID NOs 41, 42 or 49).

It is preferred with regard to the present invention that the sequence calculation according to item (b) above, further excludes the amino acid position D between $(X^6)$ and $(X^7)$ and the amino acid position W between $(X^{14})$ and $(X^{15})$, because these amino acids positions are within the RT and the n-Src loop or adjacent to these loops.

The term "serum albumin" (also referred to in the art simply as albumin) refers to a globular protein that in humans is encoded by the ALB gene. Serum albumin is the most abundant plasma protein in mammals. Serum albumin is essential for maintaining the oncotic pressure needed for proper distribution of body fluids between intravascular compartments and body tissues. It also acts as a plasma carrier by non-specifically binding several hydrophobic steroid hormones and as a transport protein for hemin and fatty acids. Furthermore, serum albumin has a very long half-life of about 19 days, and its metabolism is well-known. Albumin has also been widely used as a protein stabilizer in commercial pharmaceuticals (Sangastino et al. (2012), Blood, 120(12) 2405-2411).

SEQ ID NOs 1 and 2 as recited herein above are derived from the amino acid sequence of the SH3 domain of the human Fyn kinase (SEQ ID NO: 3). In more detail, SEQ ID NOs: 4 to 40 are derivatives of the human Fyn kinase (SEQ ID NO: 3) and SEQ ID NO: 2 is a sequence resulting from an alignment of SEQ ID NOs: 4 to 40 (cf. FIG. 8). The sequence alignment of SEQ ID NOs 4 to 40 in FIG. 8 and the examples herein below show that the amino acids listed for amino acid positions $(X^1)$ to $(X^{19})$ within the context of SEQ ID NO: 2 confer binding specificity to human serum albumin, in particular to the human serum albumin having SEQ ID NO: 46. In more detail, the sequence alignment of SEQ ID NOs 4 to 40 of the invention in FIG. 8 shows that amino acids positions ($X^1$) to ($X^{19}$) within the context of SEQ ID NO: 2 can be selected from ($X^1$) being V, T, L, H, Q, E, R, G or M; ($X^2$) being S, A, R; K, N, M, L or T; ($X^3$) being N, S, R, H, Q, F, M, K or V; ($X^4$) being T, Y, N, L, H, R, Q, W, M or E; ($X^5$) being G, S, A, E, W, L, R or K; ($X^6$) being F, Y P, W, R or Q; ($X^7$) being L or R; ($X^8$) being Q or D; ($X^9$) being N, D, A, Q, W, M or S; ($X^{10}$) being L, I or V; ($X^{11}$) being W or R; ($X^{12}$) being T or F; ($X^{13}$) being D, W, N, K, S, E or A; ($X^{14}$) being W or G; ($X^{15}$) being E or V; ($X^{16}$) being A or V; ($X^{17}$) being E, L or R; ($X^{18}$) being T, S or M; ($X^{19}$) being Y or S. Therefore, it can be expected that all possible combinations of amino acids listed for amino acid positions ($X^1$) to ($X^{19}$) in SEQ ID NO: 2 confer binding specificity to human serum albumin.

The further amino acids listed for the variant amino acid positions ($X^1$) to ($X^{19}$) within SEQ ID NO: 1 of the invention are conservative substitutions as compared to the concrete amino acids found in SEQ ID NOs 4 to 40 at positions ($X^1$) to ($X^{19}$). As further detailed below, a conservative substitution designates the substitution of an amino acid with another amino acid whose side chain has a similar biochemical property. Thus, conservative amino acid substitutions are expected not to change the overall binding properties of the polypeptide of the invention.

For example, in accordance with feature (b) herein, in the polypeptide of SEQ ID NO: 1 or 2 (or SEQ ID NOs 41, 42 or 49) additional amino acid positions outside the RT- and/or n-Src-loop of SH3 domain of the Fyn kinase and outside the amino acid positions adjacent thereto outside amino acid positions ($X^1$) to ($X^{19}$) may be exchanged or deleted, or further amino acids may be added, without substantially interfering with the binding specificity to human serum albumin. If amino acids are exchanged, conservative exchanges are preferred.

A conservative substitution comprises the substitution of an amino acid with another amino acid having a chemical property similar to the amino acid that is substituted. Preferably, the conservative substitution is a substitution selected from the group consisting of: (i) a substitution of a basic amino acid with a different basic amino acid; (ii) a substitution of an acidic amino acid with a different acidic amino acid; (iii) a substitution of an aromatic amino acid with a different aromatic amino acid; (iv) a substitution of a non-polar, aliphatic amino acid with a different non-polar, aliphatic amino acid; and (v) a substitution of a polar, uncharged amino acid with a different polar, uncharged amino acid. A basic amino acid is selected from the group consisting of arginine, histidine, and lysine. An acidic amino acid is selected from aspartate or glutamate. An aromatic amino acid is selected from the group consisting of phenylalanine, tyrosine and tryptophane. A non-polar, aliphatic amino acid is selected from the group consisting of glycine, alanine, valine, leucine, methionine, isoleucine and proline. A polar, uncharged amino acid is selected from the group consisting of serine, threonine, cysteine, asparagine and glutamine. In contrast to a conservative amino acid substitution, a non-conservative amino acid substitution is the exchange of one amino acid with any amino acid that does not fall under the above-outlined conservative substitutions (i) through (v).

Thus, also encompassed by the invention are amino acid sequences which are with increasing preference at least 90%, at least 95%, or at least 98% identical to the amino acid sequence of SEQ ID NO: 1 or 2 (or SEQ ID NOs 41, 42 or 49), wherein ($X^1$) to ($X^{19}$) are selected from the distinct amino acids shown above, or an amino acid sequence which is with increasing preference at least 90%, at least 95%, or at least 98% identical to the amino acid sequence of SEQ ID NO: 1 or 2 (or SEQ ID NOs 41, 42 or 49), wherein ($X^1$) to ($X^{19}$) are selected from the distinct amino acids shown above, and wherein the identity determination excludes amino acid positions ($X^1$) to ($X^{19}$).

SEQ ID NO: 3 is the amino acid sequence of the SH3 domain of the human Fyn kinase (aa 83-145 of Fyn kinase as reported by Kawakami et al. and Semba et al. in 1986). The amino acid sequence of Fyn SH3 is fully conserved among man, mouse, rat and monkey (gibbon). Chicken Fyn SH3 differs in one, the one of *Xenopus laevis* in two amino acid positions from the corresponding human domain. Just as other SH3 domains the Fyn SH3 is composed of two antiparallel n-sheets and contains two flexible loops (called RT and n-Src-loops) in order to interact with other proteins. In general, SH3 domains are present in a large variety of proteins participating in cellular signal transduction (Musacchio et al. (1994) Prog. Biophys. Mol. Biol. 61; 283-297). These domains do not occupy a fixed position within proteins and can be expressed and purified independently. More than 1000 occurrences of the domain are known with about 300 human SH3 domains (Musacchio A. (2003) Advances in Protein Chemistry. 61; 211-268). Although there is great sequence diversity among SH3 domains, they all share a conserved fold: a compact beta barrel formed by two antiparallel beta-sheets (Musacchio A. (2003) Advances in Protein Chemistry. 61; 211-268). Typically, SH3 domains bind to proline-rich peptides containing a PXXP core-binding motif (Ren et al. (1993) Science 259; 1157-1161), but examples of unconventional SH3 binding sites have also been described (Karkkainen et al. (2006) EMBO Rep. 7; 186-191). Most of the SH3 domains sequenced so far have an overall length of approximately 60 to 65 amino acids, but some of them may feature as many as 85 amino acids due to inserts into the loops connecting the main conservative elements of the secondary structure (Koyama et al. (1993) Cell 72(6); 945-952). An alignment of different SH3 domains revealed conserved amino acid residues responsible for the proper structure formation as well as for the canonical proline-rich motif recognition (Larson et al. (2000) Protein Science 9; 2170-2180). SEQ ID NO: 3 reads:

```
                                                (SEQ ID NO: 3)
GVTLFVALYDYEARTEDDLSFHKGEKFQILNSSEGDWWEARSLTTGETG
YIPSNYVAPVDSIQ
```

In SEQ ID NO: 3 as shown above, the sequences of the RT and the n-Src loop are underlined and double-underlined, respectively. Erpel et al. ("Mutational analysis of the Src SH3 domain: the same residues of the ligand binding surface are important for intra- and intermolecular interactions." Embo J. 14(5): 963-75, 1995) investigated the influence of mutations in the RT and n-Src loops of Src SH3 domains and demonstrated that mutations in both loops which are adjacent to the hydrophobic surface could influence the ability of this domain to participate in inter- and intramolecular associations with naturally-occurring SH3-ligands. Moreover, EP 2054432 shows that mutations in and adjacent to the RT- and/or the n-Src loop determine the binding specificity of an SH3 domain. In more detail, it was demonstrated that the Fyn SH3 domain is an attractive scaffold ("Fynomer®") for the generation of binding proteins because it (i) can be expressed in bacteria in soluble form in high amounts, (ii) is monomeric and does not aggregate when stored in solution, (iii) is very stable (Tm 70.5° C.), (iv) lacks cysteine residues, and (v) is of human origin featuring an amino acid sequence completely conserved from mouse to man and, hence, are essentially non-immunogenic (Grabulovski et al. (2007) JBC, 282, p. 3196-3204; EP 2054432). The term "Fyn SH3-derived polypeptide", used interchangeably herein with the term "Fynomer®", refers in general to a non-immunoglobulin-derived binding (poly)peptide (e.g. a so-called scaffold as described above) derived from the human Fyn SH3 domain.

In the past, the isolation of Fynomers® binding to mouse serum albumin have been described (Bertschinger J. et al., (2007), Protein Eng Des Sel, 20(2), p. 57-68 and EP 2054432). However, to the best knowledge of the inventors, so far no Fynomer®-based binders have been described in the art which bind to human serum albumin and not to unrelated proteins, such as ovalbumin (see Example 4). In addition, to the best knowledge of the inventors, so far no Fynomer®-based binders have been described in the art which bind to human serum albumin and rodent serum albumin and not to unrelated proteins, such as ovalbumin (see Example 4).

Thus, in another preferred embodiment the polypeptide of the invention further binds to rodent serum albumin and comprises or consists of an amino acid sequence selected from the group consisting of: (a)) GVTLFVALYDY($X^1$)($X^2$)($X^3$)($X^4$)($X^5$)($X^6$)D($X^7$)SFHKGEKFQIL($X^8$)($X^9$)($X^{10}$)($X^{11}$)($X^{12}$)G($X^{13}$)($X^{14}$)W($X^{15}$)($X^{16}$)RSLTTG($X^{17}$)($X^{18}$)G($X^{19}$)IPSNYVAPVDSIQ (SEQ ID NO: 41), wherein ($X^1$) is A, V, I, L, M, G, P, S, T, N, Q, C, R, H, K, D or E; ($X^2$) is R, H, K, A, V, I, L, M, G, P, S, T, N, Q or C; ($X^3$) is R, H, K, S, T, N, Q, C, F, Y, W, A, V, I, L, M, G or P; ($X^4$) is S, T, N, Q, C, A, V, I, L, M, G, P, R, H, K, F, Y or W; ($X^5$) is S, T, N, Q, C, D, E, F, Y, W, A, V, I, L, M, G, P, R, H or K; ($X^6$) is F, Y, W, A, V, I, L, M, G, P, R, H, K, S, T, N, Q or C; ($X^7$) is A, V, I, L, M, G, P, R, H or K; ($X^8$) is S, T, N, Q, C, D or E; ($X^9$) is S, T, N, Q, C, D or E; ($X^{10}$) is A, V, I, L, M, G or P; ($X^{11}$) is F, Y or W; ($X^{12}$) is S, T, N, Q or C; ($X^{13}$) is F, Y, W, R, H, K, S, T, N, Q, C, D, E, A, V, I, L, M, G or P; ($X^{14}$) is F, Y, W, A, V, I, L, M, G or P; ($X^{15}$) is D, E, A, V, I, L, M, G or P; ($X^{16}$) is A, V, I, L, M, G or P; ($X^{17}$) is D, E, A, V, I, L, M, G, P, R, H or K; ($X^{18}$) is S, T, N, Q, C, A, V, I, L, M, G or P; ($X^{19}$) is F, Y, W, S, T, N, Q or C; and (b) an amino acid sequence which is at least 90% identical to the amino acid sequence of (a), wherein the identity determination excludes amino acid positions ($X^1$) to ($X^{19}$).

According to a more preferred embodiment the polypeptide of the invention further binds to rodent serum albumin and comprises or consists of an amino acid sequence selected from the group consisting of: (a) GVTLFVALYDY($X^1$)($X^2$)($X^3$)($X^4$)($X^5$)($X^6$)D($X^7$)SFHKGEKFQIL($X^8$)($X^9$)($X^{10}$)($X^{11}$)($X^{12}$)G ($X^{13}$)($X^{14}$)W($X^{15}$)($X^{16}$)RSLTTG($X^{17}$)($X^{18}$)G($X^{19}$)IPSNYVAPVDSIQ (SEQ ID NO: 42), wherein ($X^1$) is V, T, L, H, Q, E, R, G or M; ($X^2$) is S, A, R; K, N, M, L or T; ($X^3$) is N, S, R, H, Q, F, M, K or V; ($X^4$) is T, Y, N, L, H, R, Q, W or M; ($X^5$) is G, S, A, E, W, L or R; ($X^6$) is F, Y P, W, R or Q; ($X^7$) is L or R; ($X^8$) is Q or D; ($X^9$) is N or D; ($X^{10}$) is L or I; ($X^{11}$) is W; ($X^{12}$) is T; ($X^{13}$) is D, W, N, K, S, E or A; ($X^{14}$) is W or G; ($X^{15}$) is E or V; ($X^{16}$) is A or V; ($X^{17}$) is E, L or R; ($X^{18}$) is T, S or M; ($X^{19}$) is Y or S; and (b) an amino acid sequence which is at least 90% identical to the amino acid sequence of (a), wherein the identity determination excludes amino acid positions ($X^1$) to ($X^{19}$).

In accordance with this preferred and more preferred embodiment it is preferred that positions ($X^8$) to ($X^{12}$) are either "QDLWT" (SEQ ID NO: 43) or "QNLWT" (SEQ ID NO: 44) or "DDIWT" (SEQ ID NO: 45). Positions ($X^8$) to ($X^{12}$) correspond to the n-Src-loop of the Fyn SH3 domain of SEQ ID NO: 2. As it is evident from the sequence alignment of SEQ ID NOs 4 to 32 in FIG. 8, all these polypeptides have a n-Src-loop of either "QDLWT" (SEQ ID NO: 43) or "QNLWT" (SEQ ID NO: 44) or "DDIWT" (SEQ ID NO: 45). Hence, in particular such n-Src-loop confers binding specificity to human and rodent serum albumin.

Non-limiting examples of rodents are mice, rats, squirrels, porcupines, beavers, guinea pigs, and hamsters. In another preferred embodiment the rodent is rat. In a further preferred embodiment the rodent is mouse. In a different preferred embodiment the rodent comprises mouse and rat.

According to an even more preferred embodiment the polypeptide of the invention further binds to rodent serum albumin and the amino acid sequence is selected from the amino acid sequences of SEQ ID NOs: 4 to 32.

The sequence alignment of SEQ ID NOs 4 to 32 of the invention in FIG. 8 shows that amino acids positions ($X^1$) to ($X^{19}$) within the context of SEQ ID NO: 42 can be selected from ($X^1$) being V, T, L, H, Q, E, R, G or M; ($X^2$) being S, A, R; K, N, M, L or T; ($X^3$) being N, S, R, H, Q, F, M, K or V; ($X^4$) being T, Y, N, L, H, R, Q, W or M; ($X^5$) being G, S, A, E, W, L or R; ($X^6$) being F, Y P, W, R or Q; ($X^7$) being L or R; ($X^8$) being Q or D; ($X^9$) being N or D; ($X^{10}$) being L or 1; ($X^{11}$) being W; ($X^{12}$) being T; ($X^{13}$) being D, W, N, K, S, E or A; ($X^{14}$) being W or G; ($X^{15}$) being E or V; ($X^{16}$) being A or V; ($X^{17}$) being E, L or R; ($X^{18}$) being T, S or M; and ($X^{19}$) being Y or S. Therefore, it can be expected that all possible combinations of amino acids listed for amino acid positions ($X^1$) to ($X^{19}$) in SEQ ID NO: 42 confer binding specificity to human serum albumin as well as rodent serum albumin.

The further amino acids listed for the variant amino acid positions ($X^1$) to ($X^{19}$) within SEQ ID NO: 41 of the invention are conservative substitutions as compared to the concrete amino acids found in SEQ ID NOs 4 to 32 at positions ($X^1$) to ($X^{19}$). As further detailed above, a conservative substitution designates the substitution of an amino acid with another amino acid whose side chain has a similar biochemical property. Thus, conservative amino acid substitutions are expected not to change the overall binding properties of the polypeptide of the invention.

The term "binding to a rodent serum albumin" requires that the polypeptides of the invention have a specific (in vivo and/or in vitro) binding affinity to a rodent serum albumin, and more preferably the mouse serum albumin of SEQ ID NO: 47 and the rat serum albumin of SEQ ID NO: 48. With increasing preference such polypeptides have a dissociation constant ($K_D$) to rodent serum albumin of less than 5000 nM, less than 2500 nM, and less than 1500 nM. Also such polypeptides have with increasing preference a dissociation constant ($K_D$) to any protein other than mammalian serum albumins of greater than 50000 nM, greater than 100000 nM, and greater than 500000 nM.

As discussed herein above, binding can be detected using well-known experiments in the art, such as an enzyme-linked immunosorbent assay (ELISA) or surface plasmon resonance (SPR) experiments. Such assays may preferably be performed as outlined in the examples herein below.

All polypeptides of the invention bind to human serum albumin, which is a prerequisite for being suited as a therapeutic or diagnostic for human beings. Already a dissociation constant ($K_D$) to human serum albumin of less than 5000 nM (5 μM) is believed to be sufficient to ensure that the polypeptides upon administration effectively bind to human serum albumin in vivo. For example Holt et al. (2008), Protein Engineering, Design & Selection; 21(5) 283-288, provides evidence that serum albumin serum binders having a $K_D$ in the two-digit nanomolar range as well as the one-digit micromolar range increases the serum half-life of a protein to a similar extent. Polypeptides which are cross-reactive to human serum albumin as well as rodent serum albumin are particularly advantageous, because drug discovery is facilitated. In more detail, the polypeptide may be tested in well-established and widely used animal models such as mouse and rat as well as in humans. Human (SEQ ID NO: 46) and mouse serum albumin (SEQ ID NO: 47) share an amino acid sequence identity of above 70%.

The polypeptide of the invention may bind to human serum albumin and not bind to rodent serum albumin, and comprise or consist of an amino acid sequence selected from the group consisting of: GVTLFVALYDY($X^1$)($X^2$)($X^3$)($X^4$)($X^5$)($X^6$)D($X^7$)SFHKGEKFQIL($X^8$)($X^9$)($X^{10}$)($X^{11}$)($X^{12}$)G($X^{13}$)($X^{14}$)W($X^{15}$)($X^{16}$)RSLTTG($X^{16}$)RSLTTG($X^{17}$)($X^{18}$)G($X^{19}$)IPSNYVAPVDSIQ (SEQ ID NO: 49), wherein ($X^1$) is T, H or Q; ($X^2$) is S or A; ($X^3$) is R or H; ($X^4$) is T, L, H or E; ($X^5$) is G or K; ($X^6$) is F or Y; ($X^7$) is L; ($X^8$) is D; ($X^9$) is N, D, A, Q, W, M or S; ($X^{10}$) is L, I or V; ($X^{11}$) is R; ($X^{12}$) is F; ($X^{13}$) is D; ($X^{14}$) is W; ($X^{15}$) is E; ($X^{16}$) is A; ($X^{17}$) is E; ($X^{18}$) is T; ($X^{19}$) is Y; and (b) an amino acid sequence which is at least 90% identical to the amino acid sequence of (a), wherein the identity determination excludes amino acid positions ($X^1$) to ($X^{19}$).

Furthermore, the polypeptide of the invention may bind to human serum albumin and not bind to rodent serum albumin, and the amino acid sequence may be selected from the amino acid sequences of SEQ ID NOs: 33 to 40.

The sequence alignment of SEQ ID NOs 33 to 40 of the invention in FIG. 8 shows that amino acids positions ($X^1$) to ($X^{19}$) within the context of SEQ ID NO: 49 can be selected from ($X^1$) being T, H or Q; ($X^2$) being S or A; ($X^3$) being R or H; ($X^4$) is T, L, H or E; ($X^5$) is G or K; ($X^6$) is F or Y; ($X^7$) is L; ($X^8$) is D; ($X^9$) is N, D, A, Q, W, M or S; ($X^{10}$) being L, I or V; ($X^{11}$) being R; ($X^{12}$) being F; ($X^{13}$) being D; ($X^{14}$) being W; ($X^{15}$) being E; ($X^{16}$) being A; ($X^{17}$) being E; ($X^{18}$) is T; and ($X^{19}$) is Y.

The term "does not bind to a rodent serum albumin" requires that the polypeptides of the invention do not have a specific (in vivo and/or in vitro) binding affinity to a rodent serum albumin and in particular to mouse serum albumin of SEQ ID NO: 47 and rat serum albumin of SEQ ID NO: 48. With increasing preference such polypeptides have a dissociation constant ($K_D$) to rodent serum albumin of greater than 50000 nM, greater than 75000 nM and greater than 100000 nM. Also such polypeptides preferably have a dissociation constant ($K_D$) to any protein other than mammalian serum albumins of greater than 100000 nM.

As mentioned herein above, binding can be detected using well-known experiments in the art, such as enzyme-linked as an immunosorbent assay (ELISA) or surface plasmon resonance (SPR) experiments. Such assays may preferably be performed as outlined in the examples herein below.

A further embodiment of the present invention relates to a fusion protein comprising the polypeptide of the invention fused to a pharmaceutically and/or diagnostically active protein or peptide.

In the fusion protein the polypeptide of the invention is intended to enhance the in vivo serum half-life of the pharmaceutically and/or diagnostically active protein or peptide. Hence, the pharmaceutically and/or diagnostically active protein or peptide is preferably a short-lived pharmaceutically and/or diagnostically active protein or peptide having per se with increasing preference a half-life of less than 5 days, less than 2 days, less than 1 day, less than 12 hours, less than 10 hours and less than 5 hours. For example, insulin only has a half-life of 4 to 6 min. As discussed above, serum albumin has a half-life of 19 days (Dennis et al. (2002), *J Biol Chem*, 277(38), p. 35035-35043).

The term "fusion protein" as used herein is in general terms directed to a polypeptide construct generated through the joining and expression of two or more genes which code for separate polypeptides. In other words, translation of this fusion gene results in a single polypeptide with functional properties derived from each of the original polypeptides. The polypeptides may either be directly fused or via a linker, e.g. a short peptide sequence. In general, fusion proteins are generated artificially by recombinant DNA technology well known to the skilled person (e.g. Alberts et al., Molecular Biology of the Cell, 4$^{th}$ ed. Garland Science, p. 518-519). However, polypeptides and fusion proteins of the invention may be prepared by any of the many conventional and well known techniques such as plain organic synthetic strategies, solid phase-assisted synthesis techniques or by commercially available automated synthesizers. Fusion proteins may be used in biological research or therapeutics.

A pharmaceutically active protein or peptide is a protein or peptide having a biologically activity upon administration to a subject, which brings about a beneficial effect for the subject. This term also encompasses prodrugs. A prodrug is a protein or peptide that is administered in an inactive (or less than fully active) form to a subject, and is subsequently converted to a pharmaceutically active or pharmaceutically fully active protein or peptide through metabolic processes in the subject. The pharmaceutically (fully) active protein or peptide is preferably a protein or peptide suitable for the treatment or prevention of a disease.

A diagnostically active protein or peptide is a protein or peptide having an activity upon administration to a subject, which allows to determine or identify a possible disease or disorder. A diagnostically active protein or peptide fused to a polypeptide of the invention can in particular be used to determine or identify a specific disease. For example, the location of diseased tissue within the body can be detected or identified by the polypeptide of the invention fused to the diagnostically active protein or peptide of the invention.

According to one preferred embodiment the polypeptide of the invention is directly fused to the pharmaceutically and/or diagnostically active protein or peptide.

According to another preferred embodiment the polypeptide of the invention is fused to the pharmaceutically and/or diagnostically active protein or peptide via a linker.

The fusion construct may be (directly) fused to the C- or N-terminus of the pharmaceutically and/or diagnostically active protein or peptide, more specifically by the formation of a peptide bond between the carboxy group of the C-terminal amino acid and the amino group of the N-terminal amino acid, or may be connected to the C- or N-terminus of the pharmaceutically and/or diagnostically active protein or peptide via a linker.

Suitable linkers are at the skilled person's disposal. The linker according to the invention is preferably selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Preference is also given to peptidic linkers, more specifically to oligopeptides having a length from 2 to 30 amino acids. Use of a single amino acid is also deliberately envisaged. Preferred length ranges are from 5 to 15 amino acids. Other preferred lengths are 3, 4, 6, 7, 8, 9, 10, 11, 12, 13, 14, 16, 17, 18, 19 or 20 amino acids.

Particularly preferred are linkers which are peptides which consist of at least 50%, at least 60%, at least 70%, at least 80%, at least 90% or 100% of small amino acids such as glycine, serine and alanine. Particularly preferred are linkers consisting of glycines and serines only. Most preferred are the linkers of SEQ ID NOs: 50 to 52 with special preference given to a linker being a peptide consisting of the sequence of SEQ ID NO: 52.

In accordance with a preferred embodiment the pharmaceutically and/or diagnostically active protein or peptide is selected from the group consisting of a recombinant protein, an antibody, a blood factor, a hormone, an anticoagulans, a thrombolytic, a cytokine, a chemokine, and an interferon.

Non-limiting examples of pharmaceutically and/or diagnostically active molecules which can be fused to the polypeptide of the invention binding to human serum albumin thereby prolonging their in vivo half-life comprise recombinant blood factors (such as factor VIII, factor VIIa, factor IX, thrombin, antithrombin), thrombolytics and anticoagulants (such as tissue plasminogen activator, hirudin, protein C), insulin, growth hormones (such as human growth hormone (hGH), follicle-stimulating hormone), glucagon, parathyroid hormone, calcitonin, lutropin, parathyroid hormone, thyrotrophin-alpha, choriogonadotropin-alpha, growth factors (such as erythropoetin, granulocyte colony-stimulating factor (G-CSF), granulocyte-macrophage colony-stimulating factor (GM-CSF), keratinocyte growth factor), interferons (such as interferon-alpha, interferon-beta, interferon-gamma), cytokines, chemokines, recombinant IL-1 receptor antagonist and bispecific T-cell engaging molecules (BITES).

The chemokine is preferably selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, eotaxin, Eotaxin-2, I-309, MPIF-1, 6Ckine, CTACK, MEC, lymphotactin and fractalkine.

The cytokine is preferably selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta. As it is well-known in the art, cytokines may favour a pro-inflammatory or an anti-inflammatory response of the immune system. Thus, depending on the disease to be treated either fusion constructs with a pro-inflammatory or an anti-inflammatory cytokine may be favored. For example, for the treatment of inflammatory diseases in general fusion constructs comprising anti-inflammatory cytokines are preferred, whereas for the treatment of cancer in general fusion constructs comprising pro-inflammatory cytokines are preferred.

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., 2010, Holliger and Hudson, 2005). The term "antibody" also includes embodiments such as chimeric (human constant domain, non-human variable domain), single chain and humanized (human antibody with the exception of non-human CDRs) antibodies.

Various techniques for the production of antibodies and fragments thereof are well known in the art and described, e.g. in Altshuler et al., 2010. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane (1988) and (1999) and include the hybridoma technique originally described by Köhler and Milstein, 1975, the trioma technique, the human B-cell hybridoma technique (see e.g. Kozbor, 1983; Li et al., 2006) and the EBV-hybridoma technique to produce human monoclonal antibodies (Cole et al., 1985). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, 2005). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

The antibody may be a humanized antibody. The term "humanized antibody" means, in accordance with the present invention, an antibody of non-human origin, whose protein sequences has been modified to increase its similarity to antibody variants produced naturally in humans. Creation of a humanized antibody may be accomplished, for example, by inserting the appropriate CDR coding segments (responsible for the desired binding properties), such as CDR 3 and preferably all 6 CDRs, into a human antibody "scaffold". Methods for the production of humanized antibodies are described in, e.g., EP-A1 0 239 400 and WO 90/07861.

The term "antibody light chain" designates the small polypeptide subunit of an antibody while the term "antibody heavy chain" designates the large polypeptide subunit of an antibody. A typical antibody is composed of two immunoglobulin (Ig) heavy chains and two Ig light chains. Each light chain is composed of two tandem immunoglobulin domains; one constant ($C_L$) domain and one variable domain ($V_L$) that is important for binding antigen. The heavy chain determines the class or isotype of an antibody. Each heavy chain has two regions, namely a constant region (which is the same for all immunoglobulins of the same class but differs between classes) and a variable region that differs between different B cells, but is the same for all immunoglobulins produced by the same B cell or B cell clone. The variable domain of any heavy chain is composed of a single immunoglobulin domain.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691).

The polypeptides of the invention can be fused either to the N- or C-terminus of one or more functional Fc domains or to both the N- and the C-terminus of one or more Fc domains. It is preferred that the fusion proteins of the invention comprise multimers, preferably tetramers, trimers or most preferably dimers of the polypeptides of the invention fused to at least one side, preferably to the N-terminus of one or more, preferably one Fc domain.

In accordance with a more preferred embodiment the antibody of the invention is a bispecific T-cell engaging antibody (also-called BITE® molecule).

BITE® molecules are a class of artificial bispecific fusion proteins consisting of two single-chain variable fragments (scFv), whereas one of the scFvs binds to T cells via the CD3 receptor, and the other to a tumor cell via a tumor specific molecule (Baeuerle P A. et al., (2003) Curr Opin Mol Ther., 5(4) p. 413-419; Wolf E. et al., (2005) Drug Discov Today, 10(18), p. 1237-1244). Recently, it has been reported that two BITE® antibodies are currently being tested in clinical trials (Bauerle P A and Reinhardt C., (2009), Cancer Res, 69(12), p. 4941-4944): Blinatumomab (also known as MT103) is bispecific for CD3 and CD19. It is currently being tested in a phase 1 trial in patients with late stage, relapsed non-Hodgkin's lymphoma (NHL), and in a phase 2 trial in patients with B-precursor acute lymphoblastic leukemia (B-ALL) having minimal residual disease in their bone marrow. CD19 is a surface antigen suitable to address a wide range of B-cell malignancies. The other BITE® antibody in clinical development is called MT110 and is bispecific for CD3 and epithelial cell adhesion molecule (EpCAM). It is currently being tested in a phase 1 trial with lung and gastrointestinal cancer patients. EpCAM is very frequently expressed on human adeno- and some squamous cell carcinoma, and also on cancer stem cells. Another BITE® molecule described in the literature is MT112 which is bispecific for CD3 and PSMA (Friedrich M. et al., (2012) Mol Cancer Ther., 11, p. 2664-2673). While showing excellent antitumoral efficacy, one of the major limitations often described for the BITE® molecules is their short in vivo half-life of only several hours. The short half-life of Blinatumomab and MT110, for example, makes a continuous intravenous infusion by portable minipumps for 4 to 8 weeks necessary (Bauerle P A and Reinhardt C., (2009), Cancer Res, 69(12), p. 4941-4944). More convenient administration regimens of the BITE® molecules would be beneficial for the patients.

As is evident from the Examples herein below it was surprisingly found that the fusion of a Fynomer® to a BITE® molecule (anti-albumin-CD3-PSMA) resulted in a Fynomer-BITE fusion protein with cytotoxic activity and with prolonged in vivo half-life compared to the unmodified BITE® (anti-CD3-PSMA).

The present invention relates in a further embodiment to a nucleic acid molecule encoding the polypeptide of the invention or the fusion protein of the invention.

Nucleic acid molecules, in accordance with the present invention, include DNA, such as cDNA, and mRNA. Further included are nucleic acid mimicking molecules known in the art such as synthetic or semisynthetic derivatives of DNA or RNA and mixed polymers, both sense and antisense strands. They may contain additional non-natural or derivatized nucleotide bases, as will be readily appreciated by those skilled in the art. In a preferred embodiment the polynucleotide or the nucleic acid molecule(s) is/are DNA. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

For the purposes of the present invention, a peptide nucleic acid (PNA) is a polyamide type of DNA analog. The monomeric units for the corresponding derivatives of adenine, guanine, thymine and cytosine are available commercially (for example from Perceptive Biosystems). PNA is a synthetic DNA-mimic with an amide backbone in place of the sugar-phosphate backbone of DNA or RNA. As a consequence, certain components of DNA, such as phosphorus, phosphorus oxides, or deoxyribose derivatives, are not present in PNAs.

PNA chimera according to the present invention are molecules comprising one or more PNA portions. The remainder of the chimeric molecule may comprise one or more DNA portions (PNA-DNA chimera) or one or more (poly)peptide portions (peptide-PNA chimera). Peptide-DNA chimera according to the invention are molecules comprising one or more (poly)peptide portions and one or more DNA portions. Molecules comprising PNA, peptide and DNA portions are envisaged as well. The length of a portion of a chimeric molecule may range from 1 to n−1 bases, equivalents thereof or amino acids, wherein "n" is the total number of bases, equivalents thereof and amino acids of the entire molecule.

The term "derivatives" in conjunction with the above described PNAs, (poly)peptides, PNA chimera and peptide-DNA chimera relates to molecules wherein these molecules comprise one or more further groups or substituents different from PNA, (poly)peptides and DNA. All groups or substituents known in the art and used for the synthesis of these molecules, such as protection groups, and/or for applications involving these molecules, such as labels and (cleavable) linkers are envisaged.

In those embodiments where the nucleic acid molecule comprises (rather than have) the recited sequence, additional nucleotides extend over the specific sequence either on the 5' end or the 3' end or both. Those additional sequence may be of heterologous or homologous nature and may comprise stretches of about 50 to 500 nucleotides although higher or lower values are not excluded. In the case of homologous sequences, those embodiments do not include complete genomes and are generally confined to about 1500 additional nucleotides at the 5' and/or the 3' end.

Additional heterologous sequences may include heterologous promoters which are operatively linked to the coding sequences of above molecules. Hence, preferably the nucleic acid molecule is operably linked to a promoter, and more preferably linked to a promoter selected from the group of prokaryotic promoters consisting of T5 promoter/lac operator element, T7 promotor/lac operator element, or from the group of eukaryotic promoters consisting of hEF1-HTLV, CMV enh/hFerL promoter.

The present invention also relates to a vector comprising the nucleic acid molecule of the invention.

Preferably, the vector is a plasmid, cosmid, virus, bacteriophage or another vector used e.g. conventionally in genetic engineering.

The nucleic acid molecule of the invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMT-neo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Plant expression vectors comprise pGEM-T (Promega), pCAMBIA1391 (Cambia), GATEWAY (Invitrogen), pGreen and pGreenII (PGREEN). Examples for plasmid vectors suitable for *Pichia pastoris* comprise e.g. the plasmids pAO815, pPIC9K and pPIC3.5K (all Intvitrogen).

The nucleic acid molecule referred to above may also be inserted into vectors such that a translational fusion with another polynucleotide is generated. The other polynucleotide may encode a protein which may e.g. increase the solubility, half-life and/or facilitate the purification of the fusion protein. The vectors may also contain an additional expressible polynucleotide coding for one or more chaperones to facilitate correct protein folding. For vector modification techniques, see Sambrook and Russel (2001), loc. cit. Generally, vectors can contain one or more origin of replication (ori) and inheritance systems for cloning or expression, one or more markers for selection in the host, e. g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e. g., translation initiation codon, promoters, such as naturally-associated or heterologous promoters and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Furthermore, it is preferred that the vector comprises a selectable marker. Examples of selectable markers include neomycin, ampicillin, and hygromycine, kanamycin resistance and the like. Specifically-designed vectors allow the shuttling of DNA between different hosts, such as bacteria-fungal cells or bacteria-animal cells (e. g. the Gateway® system available from Invitrogen).

An expression vector according to this invention is capable of directing the replication, and the expression, of the polynucleotide and encoded enzyme of this invention. Suitable expression vectors which comprise the described regulatory elements are known in the art.

The nucleic acid molecules as described herein above may be designed for direct introduction or for introduction via liposomes, phage vectors or viral vectors (e.g. adenoviral, retroviral) into a cell. Additionally, baculoviral systems or systems based on Vaccinia Virus or Semliki Forest Virus can be used as eukaryotic expression systems for the nucleic acid molecules of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Alternatively, the recombinant polypeptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded polypeptide. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present invention furthermore relates to an isolated cell comprising the nucleic acid molecule of the invention or the vector of the invention.

Suitable prokaryotic host cells comprise e.g. bacteria of the species *Escherichia, Bacillus, Streptomyces* and *Salmonella typhimurium*. Suitable eukaryotic host cells are e.g. fungal cells, inter alia, yeasts such as *Saccharomyces cerevisiae* or *Pichia pastoris* or insect cells such as *Drosophila* S2 and *Spodoptera* Sf9 cells and plant cells as well as mammalian cells.

Mammalian host cells that could be used include, human Hela, HEK293, H9 and Jurkat cells, mouse NIH3T3 and C127 cells, Cos 1, Cos 7 and CV1, quail QC1-3 cells, mouse L cells and Chinese hamster ovary (CHO) cells.

In a more preferred embodiment, said cell is a primary cell or primary cell line. Primary cells are cells which are directly obtained from an organism. Suitable primary cells are, for example, mouse embryonic fibroblasts, mouse primary hepatocytes, cardiomyocytes and neuronal cells as well as mouse muscle stem cells (satellite cells) and stable, immortalized cell lines derived thereof. Also within the scope of the present invention are primary mammalian cells such as mouse embryonic fibroblasts (MEF). Alternatively, the recombinant (poly)peptide can be expressed in stable cell lines that contain the gene construct integrated into a chromosome.

Appropriate culture media and conditions for the above-described host cells are well-known in the art.

The one or more host cells may be produced by introducing the one or more nucleic acid molecules or one or more vectors of the invention into the one or more host cells which upon their presence mediates the expression of the polypeptides encoded by said nucleic acid molecules or vectors. The host cells are preferably isolated host cell, meaning that the cells are not within the context of a living organism. The host may be any prokaryotic or eukaryotic cell. A suitable eukaryotic host may be a mammalian cell, an amphibian cell, a fish cell, an insect cell, a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such a human cell. The cell may be a part of a cell line.

Another embodiment of the present invention relates to a method of producing the polypeptide of any one of the invention, or the fusion protein of the invention comprising (a) culturing the isolated cell of the invention, and (b) isolating the produced polypeptide or fusion protein.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, the skilled person is also aware that these conditions may have to be adapted to the needs of the host and the requirements of the polypeptide expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycine. The cells can be kept at 37° C. in a 5% $CO_2$, water saturated atmosphere. Suitable media for insect cell culture is e.g. TNM+10% FCS or SF900 medium. Insect cells are usually grown at 27° C. as adhesion or suspension culture. Suitable expression protocols for eukaryotic cells are well known to the skilled person and can be retrieved e.g. from in Sambrook J, Russell D W, (2001), Molecular Cloning: A laboratory manual, 3rd ed, Cold Spring Harbor Laboratory Press, New York.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook J, Russell D W, (2001), Molecular Cloning: A laboratory manual. 3rd ed, Cold Spring Harbor Laboratory Press, New York.

The present invention furthermore relates to pharmaceutical and/or diagnostic composition comprising the fusion protein of any one of claims of the invention.

The pharmaceutical composition is preferably administered to mammals such as domestic and pet animals. Most preferred it is administered to humans. The pharmaceutical compositions described herein will be administered to the subject at a suitable dose.

The pharmaceutical composition for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients. Also diagnostic compositions of the invention may be manufactured in any conventional manner.

The pharmaceutical composition of the invention may be administered as the sole active ingredient or in conjunction with, e.g. as an adjuvant to or in combination with, other drugs, e.g. immunosuppressive or immune modulating agents or other anti-inflammatory agents.

Pharmaceutical compositions of the invention preferably comprise a pharmaceutically acceptable carrier or excipient. By "pharmaceutically acceptable carrier or excipient" is meant a non-toxic solid, semisolid or liquid filler, diluent, encapsulating material or formulation auxiliary of any type. Examples of pharmaceutically acceptable carriers or excipients are described, e.g., in Ansel et al., "Pharmaceutical Dosage Forms and Drug Delivery Systems", 7th edition, Lippincott Williams & Wilkins Publishers, 1999.

The diagnostic composition of the invention is useful in the detection of an undesired physiological condition or a disease. Accordingly, the diagnostic composition of the invention may be used for assessing the onset or the disease status and in particular a disease state. The diagnostic composition of the invention can be administered as sole active agent or can be administered in combination with other agents, if the diagnostic composition is, for example, used to identify sites of undesired physiological condition or a disease.

The present invention furthermore relates to a kit comprising the fusion protein of the invention, wherein the fusion protein comprises a diagnostically active protein or peptide.

The various components of the kit may be packaged in one or more containers such as one or more vials. The vials may, in addition to the components, comprise preservatives or buffers for storage. In addition, the kit may contain instructions for use.

Figure 1:
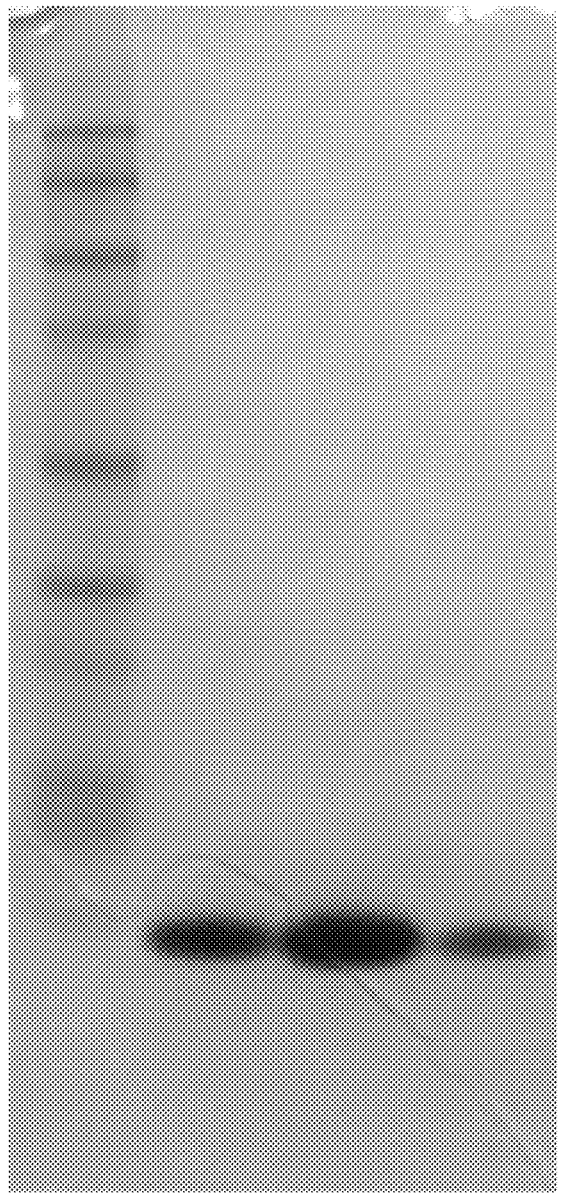
FIG. 1 shows the SDS-PAGE characterization of albumin-binding polypeptides of the invention: Lane M: molecular weight standard; Lane A: Fynomer® C1 (SEQ ID NO: 4); Lane B: Fynomer® 17H (SEQ ID NO: 5); Lane C: WT Fyn-SH3 (SEQ ID NO: 3).

The examples illustrate the invention.

EXAMPLE 1: FYN SH3 DERIVED POLYPEPTIDES BIND TO HUMAN SERUM ALBUMIN

Methods
1) Lysate ELISA on Human Serum Albumin Protein

Using the Fynomer® phage libraries described in Schlatter et al. (Schlatter et al. (2012) mAbs, 4(4) p. 497-50) Fyn-SH3 derived binding proteins specific to human serum albumin were isolated using human serum albumin (Sigma-Aldrich, cat. no A3782) and serum albumin from a rodent species (rat serum albumin, Sigma-Aldrich, cat. no A6414) as antigens and standard phage display as selection technology (Grabulovski D. et al., (2007) J Biol Chem 282, p. 3196-3204, Viti, F. et al. (2000) Methods Enzymol. 326, 480-505).

After naïve and affinity maturation selections, enriched Fyn SH3-derived polypeptides were screened for binding to human serum albumin and/or serum albumin from a rodent species (mouse/rat) by lysate ELISA. DNA encoding the Fyn SH3-derived binding proteins was cloned into the bacterial expression vector pQE12 (Qiagen) so that the resulting constructs carried a C-terminal myc-hexahistidine tag as described in Grabulovski et al. (Grabulovski et al. (2007) JBC, 282, p. 3196-3204). The polypeptides were expressed in the cytosol of E. coli bacteria in a 96-well format and 200 µl of cleared lysate per well was prepared essentially as described in Bertschinger et al. (Bertschinger et al. (2007) Protein Eng Des Sel 20(2): p. 57-68). Briefly, transformed bacterial colonies were picked from agar plates and grown in a round bottom 96-well plate (Nunc, cat. no. 163320) in 200 µl 2×YT medium containing 100 µg/ml ampicillin and 0.1% (w/v) glucose. Protein expression was induced after growth for 3 h at 37° C. and 200 r.p.m. by adding 1 mM IPTG (Applichem, Germany). Proteins were expressed overnight in a rotary shaker (200 r.p.m., 30° C.). Subsequently, the 96-well plate was centrifuged at 1800 g for 10 min and the supernatant was discarded. The bacterial pellets were resuspended in 65 µl Bugbuster containing Benzonase Nuclease (VWR, cat. No. 70750-3) and incubated at RT for 30 minutes. Afterwards, the monoclonal bacterial lysates were cleared by centrifugation (1800 g for 10 min), diluted with 170 µL PBS and filtered using a multiscreen filter plate (0.45 µm pore size; Millipore cat. No. MSHVN4510). Monoclonal bacterial lysates were used for ELISA: human serum albumin was immobilized on maxisorp F96 wells (Nunc, cat. no 439454) overnight at room temperature. Plates were then blocked with PBS, 4% (w/v) milk (Rapilait, Migros, Switzerland). Subsequently, 20 µl of PBS, 10% milk containing 25 µg/ml anti-myc antibody 9E10 and 80 µl of bacterial lysate were applied (resulting in a final anti-myc antibody concentration of 5 µg/ml). After incubating for 1 h and washing, bound Fyn SH3-derived polypeptides were detected with anti-mouse-HRP antibody conjugate (Sigma) at a final concentration of 5 µg/ml. The detection of peroxidase activity was done by adding 100 µL per well BM blue POD substrate (Roche) and the reaction was stopped by adding 50 µl 1 M $H_2SO_4$. The DNA sequence of the specific binders was verified by DNA sequencing. Cross-reactivity towards serum albumin from a rodent species was detected by monoclonal lysate ELISA using mouse serum albumin (Sigma-Aldrich, cat. no A3139) as an antigen and the protocol described above. Alternatively, cross-reactivity towards mouse and rat serum albumin was confirmed surface plasmon resonance experiments (see below).

2) Expression and Purification of Fyn SH3-Derived Polypeptides in E. coli

Fyn SH3-derived albumin-binding polypeptides were expressed in the cytosol of TG1 E. coli bacteria as well as purified as described in Grabulovski et al. (Grabulovski et al. (2007) JBC, 282, p. 3196-3204).

3) Affinity Measurements

Affinity measurements were performed using a Biacore T200 instrument (GE Healthcare). For the interaction analysis between serum albumin, derived from mouse, rat or human, and Fyn SH3-derived albumin-binding polypeptides, a Series S CM5 chip (GE Healthcare) was used with albumin proteins immobilized using the amine coupling kit (GE healthcare). Serum albumin proteins from different species (mouse, rat or human) were immobilized (2000-3000 RU) on different flow cells of the chip whereas a blank-immobilized flow cell served as a reference flow cell. The running buffer was PBS containing 0.05% Tween 20 at pH 7.4. The interactions were measured at a flow of 30 μl/min and 25° C. and different concentrations of Fyn SH3-derived albumin-binding polypeptides were injected. All kinetic data of the interaction was evaluated using Biacore T200 evaluation software.

Results

1) The amino acid sequences of ELISA positive Fyn SH3-derived polypeptides binding to human serum albumin is presented in SEQ ID NOs: 4 to 40 as appended in the sequence listing. In addition, Fyn SH3-derived polypeptides (SEQ ID NOs: 4 to 32) also showed binding to mouse serum albumin as confirmed by lysate ELISA and/or Biacore affinity measurements.

2) The expression yields of two selected Fyn SH3-derived albumin-binding polypeptides of the invention from bacterial cultures under non-optimized conditions in shake flasks is depicted in Table 1. The yield was in the same range as the expression yield of the WT Fyn-SH3 polypeptide. High protein-purity was confirmed by SDS-PAGE analysis and the gel is depicted in FIG. 1.

TABLE 1

Expression yields of Fyn SH3-derived albumin-binding polypeptides produced in TG1 E. coli bacteria

| Fynomer ® | SEQ ID NO. | Yield (mg/l) |
| --- | --- | --- |
| 17H | 5 | 10 |
| C1 | 4 | 25 |
| WT Fyn-SH3 | 3 | 10 |

3) The binding properties were analyzed by real-time interaction analysis on a Biacore chip revealing the following dissociation constants ($K_D$) for selected albumin-binding polypeptides against albumin derived from either rat (RSA), mouse (MSA) or human (HSA) (depicted in Table 2).

TABLE 2

Dissociation constants of Fyn SH3-derived serum albumin-binding polypeptides to RSA, MSA and HSA.

| Fynomer ® | SEQ ID NO. | $K_D$ (nM) RSA | $K_D$ (nM) MSA | $K_D$ (nM) HSA |
| --- | --- | --- | --- | --- |
| C1 | 4 | 72 | 408 | 1290 |
| 17H | 5 | 17 | 96 | 455 |

EXAMPLE 2: ALBUMIN-BINDING FYN SH3 DERIVED POLYPEPTIDES HAVE A PROLONGED SERUM HALF-LIFE IN MICE

Methods

The pharmacokinetic profile of albumin-binding Fyn-SH3 derived polypeptides was investigated in BALB/c mice (Charles River) and compared to the WT Fyn-SH3 molecule. Fynomer® C1 (SEQ ID NO: 4), Fynomer® 17H (SEQ ID NO: 5) and WT Fyn-SH3 (SEQ ID NO: 3) were radiolabeled using Iodine-125 (Perkin Elmer cat no. NEZ033A001MC) and Chloramine T (Sigma-Aldrich cat NO 31224). The labeling reaction was carried out for two minutes at room temperature before removal of labeling reagents using PD MiniTrap G-25 columns (GE Healthcare cat. no 28-9180-07). Three BALB/c mice were injected i.v. with 13.5 μg of either radiolabeled Fynomer® C1 (SEQ ID NO: 4), Fynomer® 17H (SEQ ID NO: 5) or WT Fyn-SH3 (SEQ ID NO: 3). After 10 minutes, 2.5, 4, 6, 9, 25, 35 hours, blood was collected into EDTA coated microvettes (Sarstedt) and centrifuged for 10 min at 9300 g. Radioactivity was counted by mixing the serum with Supermix Perkin Elmer Scintillation Fluid and quantification of beta-emission of each sample with a 1450 MicroBeta Trilux scintillation counter and serum levels were calculated (results expressed as % injected dose (ID)/ml of blood). From the serum levels of Fynomer® C1, Fynomer® 17H and WT Fyn-SH3 determined in serum at different time points and the resulting slope k of the elimination phase (plotted in a semi-logarithmic scale), the half-lives were calculated using the formula $t_{1/2}=\ln 2/-k$.

Results

As depicted in Table 3, Fynomer® C1 (SEQ ID NO: 4) and Fynomer® 17H (SEQ ID NO: 5) show a significantly better terminal half-life as the WT Fyn-SH3 protein (SEQ ID NO: 3). Time-points used for half-life calculation: Fynomer® C1 and Fynomer® 17H: 2.5-35 h; WT Fyn-SH3: 2.5-25 h)

TABLE 3

Terminal half-life of Fyn SH3-derived serum albumin-binding polypeptides in mice compared to the WT Fyn-SH3 protein.

| Fynomer ® | SEQ ID NO: | $t_{1/2}$ (h) |
| --- | --- | --- |
| C1 | 4 | 10.5 |
| 17H | 5 | 21.3 |
| WT Fyn-SH3 | 3 | 4.4 |

EXAMPLE 3: ALBUMIN-BINDING FYN SH3 DERIVED POLYPEPTIDES CAN EXTEND SERUM HALF-LIFE OF BITE® Molecules Methods:

1) Expression and Purification of an Albumin Binding Fyn-SH3 Fusion Protein

Figure 2:
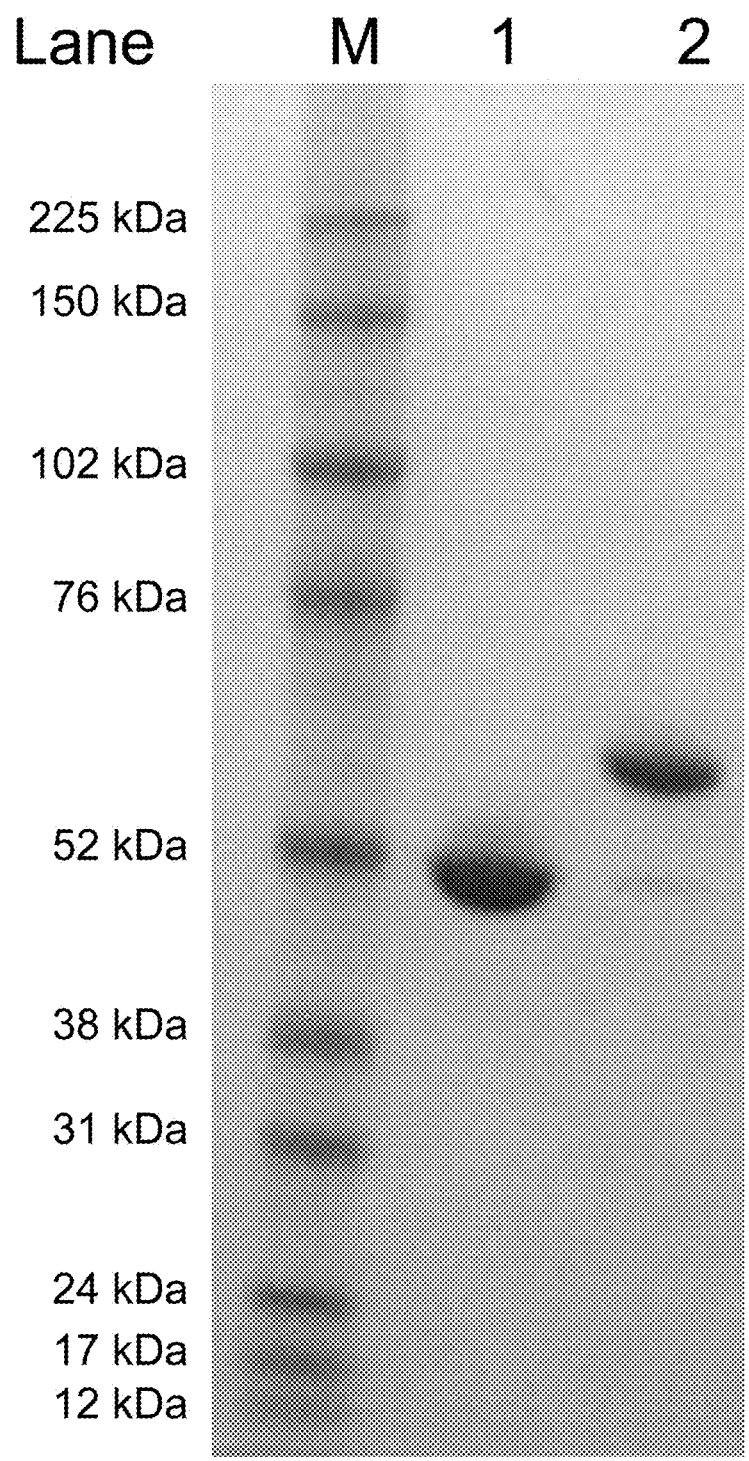
FIG. 2 shows the SDS-PAGE characterization of the unmodified BITE® polypeptide (SEQ ID NO: 53, lane 1) and the Fynomer®-BITE® fusion protein COVA406 (SEQ ID NO: 54, lane 2), consisting of the albumin binding Fynomer® 17H and the BITE® molecule. The molecular weight standard is shown in Lane M.

The Fynomer® 17H (Seq ID NO: 5) has been genetically fused to the N-terminus of the CD3-PSMA specific BITE® (Seq ID NO: 53) via a 15 amino acid linker (linker SEQ ID NO: 52) yielding the trispecific anti-albumin/PSMA/CD3 protein COVA406 (SEQ ID NO: 54). The BITE® protein (SEQ ID NO: 53) and the fusion molecule of the invention COVA406 (SEQ ID NO: 54) carrying a C-terminal penta-his-tag were transiently transfected into FreeStyle CHO—S cells and expressed in serum-free/animal component-free media for 6 days. The proteins were purified from the supernatants by Protein L affinity chromatography (Thermo Scientific, cat. No. 89928) with an ÄKTA Purifier instrument (GE Healthcare). Concentrations were determined by absorbance measurement at 280 nm. Yields are listed in Table 4. The SDS PAGE of both proteins is shown in FIG. 2.

Figure 3:
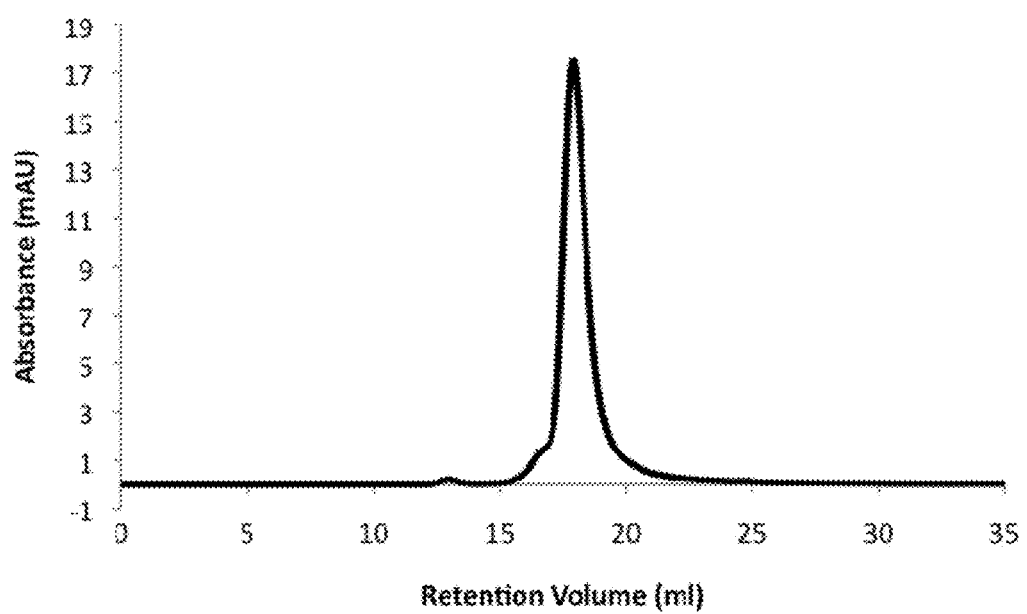
FIG. 3 shows the size exclusion chromatogram (SEC) of COVA406 (SEQ ID NO: 54).

After purification size exclusion chromatography has been performed with COVA406 using an ÄKTA FPLC system and a Superdex G200, 30/100 GL column (GE Healthcare) (see FIG. 3).

2) FACS Binding Experiment with a BITE® Fusion Protein of the Invention

The polypeptide COVA406 (SEQ ID NO: 54, final concentration 300 nM) was mixed with 100 µl cell suspension containing either (i) 1×10$^5$ Jurkat E6-1 cells (CD3 positive cells), (ii) 1×10$^5$ 22 Rv1 prostate carcinoma cells (PSMA positive cells) or (iii) 1×10$^5$ LS174T colorectal adenocarcinoma cells (PSMA and CD3 negative, ATCC cat. No. CL-188) in PBS/1% BSA/0.2% sodium azide. As a negative control, the same cells were incubated with PBS/1% BSA/ 0.2% sodium azide instead of COVA406 (PBS control). After 60 min incubation on ice, cells were washed, and bound protein was detected by incubation with 10 µg/ml mouse anti tetra-HIS antibody (Qiagen, cat no. 34670), followed by incubation with anti-mouse IgG-Alexa488 conjugate (Invitrogen) at a concentration of 10 ug/mL. Finally cells were washed three times and stained cells were then analyzed on a Guava EasyCyte™ (Millipore) flow cytometer.

3) Redirected T-Cell Mediated Cell Cytotoxicity Analysis

The polypeptide COVA406 (SEQ ID NO: 54) was tested in a redirected T-cell mediated cell cytotoxicity assay using a protocol adapted from Dreier et. al. (2002) Int. J. Cancer: 100, 690-697.

Human PBMCs were used as effector cells. On the day before the experiment PBMCs were isolated from fresh buffy coat preparations by Ficoll Plaque plus (GE Healthcare) and density gradient centrifugation using standard procedures. Isolated PBMCs were then incubated over night at a cell concentration of 4×10$^6$ cells/ml in 10% FCS, RPMI and 37° C., 5% CO$_2$.

For the cell kill experiment PBMCs were centrifuged and resuspended in 10% FCS, RPMI at a cell concentration of 2.5×10$^7$ cells/ml.

Target cells were labeled with Calcein AM by incubating cells at a final Calcein AM concentration of 10 µM for 30 min at 37° C., 5% CO$_2$. Subsequently excess dye was removed by washing cells twice with approx. 15 mL Medium. Finally target cell number was adjusted to 1*10$^6$ cells/ml. Target tumor cells were either 22Rv1 cells (PSMA positive, ATCC cat. No. CRL-2505) or HT29 colon carcinoma cells (PSMA negative, DSMZ cat. No. ACC-299).

Effector molecules were diluted in 10% FCS, RPMI to a maximum concentration of 1200 ng/mL. A dilution series of 1/10 dilutions was prepared.

Finally target cell suspension, effector cell suspension and the different concentrations of the polypeptide COVA406 (SEQ ID NO: 54) were then mixed in equal amounts. A total of 50000 target cells were added per well and the effector to target cell ratio was 25/1, The final maximal concentration of effector molecules was 400 ng/µl. Cell lysis was measured after 5 hours incubation at 37° C. and 5% CO$_2$. After incubation, the cell suspension was centrifuged and cell lysis was quantified by detection of Calcein AM fluorescence in the supernatant using a fluorescence reader.

The amount of redirected cell lysis was normalized to the maximum lysis control (cells lysed by the addition of 1% Triton X-100) and spontaneous lysis (target cells incubated with PMBCs in the absence of effector molecules). Percentage of cell lysis was calculated according to the following formula:

% lysis=(((fluorescence sample)−(fluorescence spontaneous lysis control))/((fluorescence maximum lysis control)−(fluorescence spontaneous lysis control)))×100

All measurements were done in triplicates. Specific cell lysis was plotted versus the concentration of COVA406 and evaluated using Prism 5 (GraphPad Software) by fitting a sigmoidal dose-response.

4) Comparison of the Pharmacokinetic Profiles of COVA406 and the BITE® Molecule

The pharmacokinetic profile of COVA406 in C57BL/6 mice (Charles River) was investigated and compared to the parental BITE® molecule. Five C57BL/6 mice were injected i.v. each with 48 µg COVA406 (SEQ ID NO: 54) or BITE® (SEQ ID NO: 53). After 10 and 30 min, 1, 3, 5, 7, 9, 12, 24, 28, 33 and 48 hours, blood was collected into EDTA coated microvettes (Sarstedt), centrifuged for 10 min at 9300 g and the serum levels of COVA406 or BITE® were determined by ELISA. Briefly, black maxisorp microtiter plates (Nunc) were coated with 10 µg/ml of a peptide derived from CD3 (Sequence: QDGNEEMGGITQTPYKV-SISGTTVILT; SEQ ID NO: 55) (expressed as Fc-fusion) and incubated over night at 4° C. After blocking with 4% milk (Rapilait, Migros, Switzerland) in PBS, serum samples at appropriate dilutions were applied, resulting in a final buffer concentration of 2% mouse serum (Sigma) and 4% milk. After incubation for 1 hr, wells were washed with PBS, and bound COVA406 or BITE® were detected with Penta-His-biotin (Qiagen) followed by Streptavidin-HRP conjugate (Sigma). The assay was developed with QuantaRed fluorogenic substrate (Pierce). The reaction was stopped after 3 min incubation and the fluorescence intensity was measured at 544 nm (excitation) and 590 nm (emission). The serum levels of COVA406 and BITE® were determined using a standard curve of COVA406 and BITE® (diluted to 333—0.5 ng/ml each). From the concentrations of COVA406 and BITE® determined in serum at different time points and the resulting slope k of the elimination phase (plotted in a semi-logarithmic scale), the half-lives were calculated using the formula $t_{1/2}$=ln 2/−k. Timepoints used for half-life calculation: COVA406: 1-48 h; BITE®: 1-12 h.

Result:

COVA406 (SEQ ID NO: 54) expressed with a similar yield as the BITE® molecule (SEQ ID NO: 53) (Table 4).

TABLE 4

Purification yields of the BITE ® and Fyn-SH3 derived albumin-binding polypeptide fusions produced in transiently transfected CHO-S cells.

| | SEQ ID NO: | Yield (mg/l) |
|---|---|---|
| BITE ® | 53 | 8.1 |
| COVA406 | 54 | 5.0 |

Figure 4:
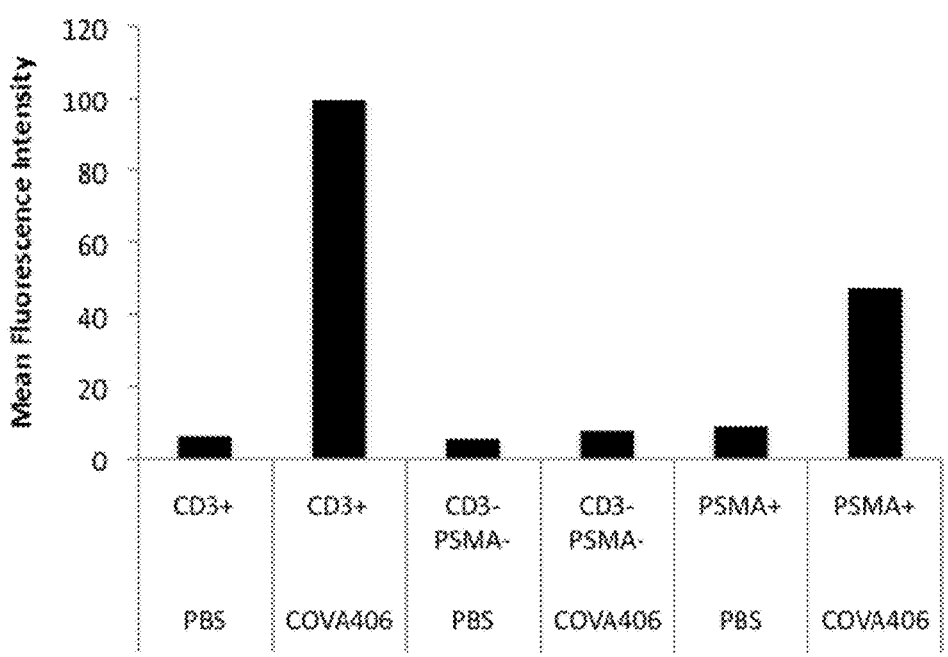
FIG. 4 depicts a FACS binding experiment with COVA406 (SEQ ID NO: 54) using cells expressing CD3 (Jurkat E6-1), cells expressing PSMA (22Rv1 cells) and an irrelevant cell line expressing neither CD3 nor PSMA (LS174T cells). Binding is expressed as mean fluorescence intensity. CD3+: CD3-positive cells; CD3−: CD3-negative cells; PSMA+: PSMA-positive cells; PSMA−: PSMA-negative cells; COVA406: COVA406 is used as binding reagent; PBS: negative control, phosphate buffered saline is added instead of COVA406. COVA406 recognizes both antigens CD3 and PSMA expressed on cells.
Figure 5:
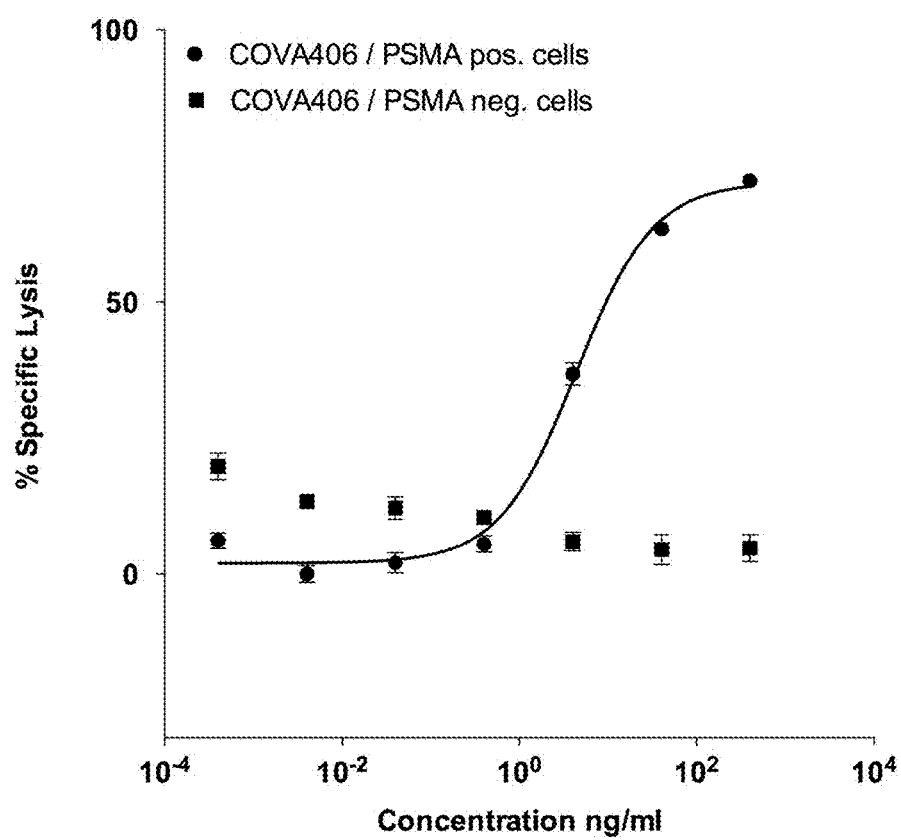
FIG. 5 depicts the analysis of redirected cell lysis of PSMA positive cells (22Rv1 cells) or PSMA negative cells (HT29 cells) by COVA406 (SEQ ID NO: 54) using human PBMCs as effector cells. The target cells 22Rv1 and HT29 were pre-labeled with Calcein AM and then incubated with human PBMCs (at effector cell to target cell ratio (E:T) of 25:1) and different concentrations of COVA406 (SEQ ID NO: 54) for 5 hours. The percentage of specific tumor cell lysis was measured by detection of calcein-release into the supernatant. Triplicates of 3 wells are shown ±SEM.
Figure 6:
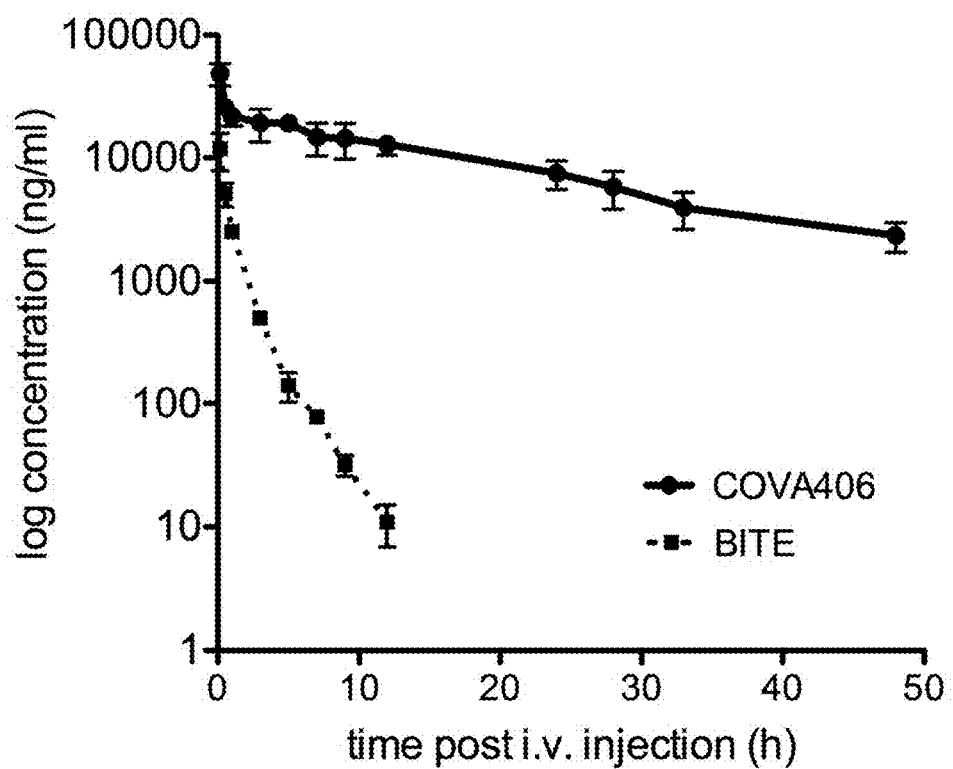
FIG. 6 shows the serum concentrations of COVA406 (SEQ ID NO: 54) and the BITE® protein (SEQ ID NO: 53) at different time-points after a single i.v. injection into C57BL/6 mice. The concentration in serum was determined by ELISA. Mean values of 5 mice are shown ±SD FIG. 7 Specificity ELISA of prior art Fyn SH3 variants isolated after affinity selections. MSA=mouse serum albumin, HSA=human serum albumin, RSA=rat serum albumin, BSA=bovine serum albumin FIG. 8 Sequence alignment of SEQ ID NOs 4 to 40.

The size exclusion chromatography (SEC) profile after purification demonstrated that COVA406 eluted as a single, monomeric peak showing that the fusion protein has excellent biophysical properties (FIG. 3). Specific binding to PSMA-positive cells (22Rv1 cells) and CD3-positive cells (Jurkat E6-1, CD3 positive) was validated in a FACS experiment. Mean fluorescence intensities (MFI) of the stainings are depicted in FIG. 4. Redirected T-cell mediated cell cytotoxicity was validated in a Calcein release assay using PBMCs as effector cells. Specific redirected cell-lysis of PSMA-positive cells with COVA406 ($EC_{50}$=4.35 ng/ml) is shown in FIG. 5. Cells with no PSMA expression (HT29 cells) were not lysed under the same conditions, showing that COVA406 is able to kill specifically PSMA positive cells. An improved pharmacokinetic profile of COVA406 (SEQ ID NO: 54) compared to the BITE® protein (SEQ ID NO: 53) was observed in mice. FIG. 6 shows the serum concentrations (ng/ml) and terminal elimination phase of COVA406 and the parental BITE®. COVA406 shows a significantly better half-life (14.3 hours) compared to the BITE® (1.5 hours). This example shows that serum albumin binding proteins of the invention are able to prolong the in vivo half-life of otherwise short-lived molecules, in particular of BITE® molecules.

EXAMPLE 4: PRIOR ART FYNOMERS® WHICH BIND TO SERUM ALBUMIN

For Material and Methods, see Publications EP2054432 and "Grabulovski, Dragan: The SH3 domain of fyn kinase as a scaffold for the generation of new binding proteins. ETH Dissertation Nr 17216 (May 2007). www.dx.doi.org/10.3929/ethz-a-005407897".

Figure 7:
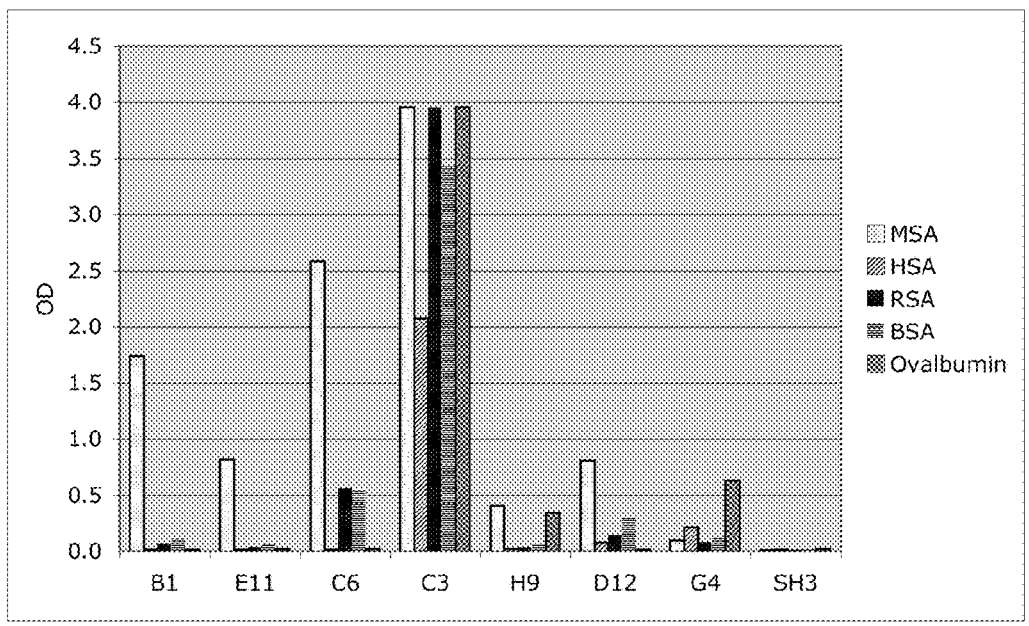

FIG. 7 shows specificity ELISA of Fyn SH3 variants isolated after affinity selections. None of the Fynomers® binds to HSA or HSA/rodent serum albumin, except for C3. However, C3 cross-reacts also with the non-related ovalbumin (hen egg white albumin). Therefore, C3 is considered as an unspecific binding protein.

The invention claimed is:

1. A polypeptide binding to human serum albumin, wherein the polypeptide comprises an amino acid sequence selected from the group consisting of: SEQ ID Nos: 4 to 40.

2. The polypeptide of claim 1, wherein the amino acid sequence is selected from the amino acid sequences of SEQ ID NOs: 4, 5 or 6 to 32.

3. A fusion protein comprising the polypeptide of any one of claims 1 or 2 fused to a pharmaceutically and/or diagnostically active protein or peptide.

4. The fusion protein of claim 3, wherein the polypeptide is directly fused to the pharmaceutically and/or diagnostically active protein or peptide.

5. The fusion protein of claim 3, wherein the polypeptide is fused to the pharmaceutically and/or diagnostically active protein or peptide via a linker.

6. The fusion protein of claim 3, wherein the pharmaceutically and/or diagnostically active protein or peptide is selected from the group consisting of a recombinant protein, an antibody, a blood factor, a hormone, an anticoagulans, a thrombolytic, a cytokine, a chemokine, and an interferon.

7. The fusion protein of claim 5, wherein the antibody is a bispecific T-cell engaging antibody.

8. A pharmaceutical and/or diagnostic composition comprising the fusion protein of claim 3.

* * * * *

```
                           SEQUENCE LISTING

<160> NUMBER OF SEQ ID NOS: 55

<210> SEQ ID NO 1
<211> LENGTH: 64
<212> TYPE: PRT
<213> ORGANISM: Artificial
<220> FEATURE:
<223> OTHER INFORMATION: derivative SH3 domain of the Fyn kinase
<220> FEATURE:
<221> NAME/KEY: Variant
<222> LOCATION: 12
<223> OTHER INFORMATION: Wherein Xaa can be Alanine; Valine; Isoleucine;
      Leucine; Methionine; Glycine; Proline; Serine; Threonine;
      Asparagine; Glutamine; Cysteine;Arginine; Histidine; Lysine;
      Aspartic Acid or Glutamic Acid
<220> FEATURE:
<221> NAME/KEY: Variant
<222> LOCATION: 13
<223> OTHER INFORMATION: Wherein Xaa can be Arginine; Histidine; Lysine;
      Alanine; Valine; Isoleucine;Leucine; Methionine; Glycine; Proline;
      Serine; Threonine;Asparagine; Glutamine or Cysteine
<220> FEATURE:
<221> NAME/KEY: Variant
<222> LOCATION: 14
<223> OTHER INFORMATION: Wherein Xaa can be Arginine; Histidine; Lysine;
      Serine; Threonine; Asparagine; Glutamine; Cysteine; Phenylalanine;
      Tyrosine; Tryptophan;Alanine; Valine; Isoleucine;Leucine;
      Methionine; Glycine or Proline
<220> FEATURE:
<221> NAME/KEY: Variant
<222> LOCATION: 15
<223> OTHER INFORMATION: Wherein Xaa can be any one of the naturally
      occurring amino acids
<220> FEATURE:
<221> NAME/KEY: Variant
<222> LOCATION: 16
<223> OTHER INFORMATION: Wherein Xaa can be any one of the naturally
      occurring amino acids
<220> FEATURE:
<221> NAME/KEY: Variant
<222> LOCATION: 17
<223> OTHER INFORMATION: Wherein Xaa can be Phenylalanine; Tyrosine;
      Tryptophan; Alanine; Valine; Isoleucine; Leucine; Methionine;
      Glycine; Proline; Arginine; Histidine; Lysine; Serine; Threonine;
      Asparagine; Glutamine or Cysteine
<220> FEATURE:
<221> NAME/KEY: Variant
<222> LOCATION: 19
<223> OTHER INFORMATION: Wherein Xaa can be Alanine; Valine; Isoleucine;
      Leucine; Methionine; Glycine; Proline; Arginine; Histidine or
      Lysine
<220> FEATURE:
<221> NAME/KEY: Variant
<222> LOCATION: 31
<223> OTHER INFORMATION: Wherein Xaa can be Serine, Threonine;
      Asparagine; Glutamine;Cysteine;Aspartic Acid or Glutamic Acid
<220> FEATURE:
<221> NAME/KEY: Variant
<222> LOCATION: 32
<223> OTHER INFORMATION: Wherein Xaa can be Serine; Threonine;
      Asparagine; Glutamine; Cysteine;Aspartic Acid; Glutamic Acid;
      Alanine; Valine; Isoleucine; Leucine; Methionine;
      Glycine; Proline;Phenylalanine;Tyrosine or Tryptophan
```

-continued

```
<220> FEATURE:
<221> NAME/KEY: Variant
<222> LOCATION: 33
<223> OTHER INFORMATION: Wherein Xaa can be Alanine; Valine; Isoleucine;
      Leucine; Methionine;Glycine or Proline
<220> FEATURE:
<221> NAME/KEY: Variant
<222> LOCATION: 34
<223> OTHER INFORMATION: Wherein Xaa can be Phenylalanine; Tyrosine;
      Tryptophan; Arginine; Histidine or Lysine
<220> FEATURE:
<221> NAME/KEY: Variant
<222> LOCATION: 35
<223> OTHER INFORMATION: Wherein Xaa can be Serine; Threonine;
      Asparagine; Glutamine; Cysteine; Phenylalanine; Tyrosine or
      Tryptophan
<220> FEATURE:
<221> NAME/KEY: Variant
<222> LOCATION: 37
<223> OTHER INFORMATION: Wherein Xaa can be any one of the naturally
      occurring amino acids
<220> FEATURE:
<221> NAME/KEY: Variant
<222> LOCATION: 38
<223> OTHER INFORMATION: Wherein Xaa can be Phenylalanine; Tyrosine;
      Tryptophan; Alanine; Valine; Isoleucine; Leucine; Methionine;
      Glycine or Proline
<220> FEATURE:
<221> NAME/KEY: Variant
<222> LOCATION: 40
<223> OTHER INFORMATION: Wherein Xaa can be Aspartic Acid; Glutamic
      Acid; Alanine; Valine; Isoleucine;Leucine; Methionine; Glycine
      or Proline
<220> FEATURE:
<221> NAME/KEY: Variant
<222> LOCATION: 41
<223> OTHER INFORMATION: Wherein Xaa can be Alanine; Valine; Isoleucine;
      Leucine; Methionine; Glycine or Proline
<220> FEATURE:
<221> NAME/KEY: Variant
<222> LOCATION: 48
<223> OTHER INFORMATION: Wherein Xaa can be Aspartic Acid; Glutamic
      Acid; Alanine; Valine; Isoleucine;Leucine; Methionine; Glycine;
      Proline; Arginine; Histidine or Lysine
<220> FEATURE:
<221> NAME/KEY: Variant
<222> LOCATION: 49
<223> OTHER INFORMATION: Wherein Xaa can be Serine; Threonine;
      Asparagine; Glutamine; Cysteine; Alanine; Valine; Isoleucine;
      Leucine; Methionine; Glycine or Proline
<220> FEATURE:
<221> NAME/KEY: Variant
<222> LOCATION: 51
<223> OTHER INFORMATION: Wherein Xaa can be Phenylalanine; Tyrosine;
      Tryptophan; Serine; Threonine; Asparagine; Glutamine or Cysteine

<400> SEQUENCE: 1

Gly Val Thr Leu Phe Val Ala Leu Tyr Asp Tyr Xaa Xaa Xaa Xaa Xaa
1               5                   10                  15

Xaa Asp Xaa Ser Phe His Lys Gly Glu Lys Phe Gln Ile Leu Xaa Xaa
            20                  25                  30

Xaa Xaa Xaa Gly Xaa Xaa Trp Xaa Xaa Arg Ser Leu Thr Thr Gly Xaa
        35                  40                  45

Xaa Gly Xaa Ile Pro Ser Asn Tyr Val Ala Pro Val Asp Ser Ile Gln
    50                  55                  60

<210> SEQ ID NO 2
<211> LENGTH: 64
<212> TYPE: PRT
<213> ORGANISM: Artificial
<220> FEATURE:
<223> OTHER INFORMATION: derivative SH3 domain of the Fyn kinase
<220> FEATURE:
<221> NAME/KEY: Variant
```

```
<222> LOCATION: 12
<223> OTHER INFORMATION: Wherein Xaa can be Valine; Threonine; Leucine;
      Histidine; Glutamine; Glutamic Acid;Arginine;Glycine or Methionine
<220> FEATURE:
<221> NAME/KEY: Variant
<222> LOCATION: 13
<223> OTHER INFORMATION: Wherein Xaa can be Serine; Alanine; Arginine;
      Lysine, Asparagine; Methionine;Leucine or Threonine
<220> FEATURE:
<221> NAME/KEY: Variant
<222> LOCATION: 14
<223> OTHER INFORMATION: Wherein Xaa can be Asparagine; Serine;
      Arginine; Histidine; Glutamine; Phenylalanine;Methionine;
      Lysine or Valine
<220> FEATURE:
<221> NAME/KEY: Variant
<222> LOCATION: 15
<223> OTHER INFORMATION: Wherein Xaa can be Threonine; Tyrosine;
      Asparagine; Leucine;Histidine; Arginine;Glutamine;Tryptophan;
      Methionine or Glutamic Acid
<220> FEATURE:
<221> NAME/KEY: Variant
<222> LOCATION: 16
<223> OTHER INFORMATION: Wherein Xaa can be Glycine; Serine; Alanine;
      Glutamic Acid;Tryptophan; Leucine;Arginine or Lysine
<220> FEATURE:
<221> NAME/KEY: Variant
<222> LOCATION: 17
<223> OTHER INFORMATION: Wherein Xaa can be Phenylalanine; Tyrosine;
      Proline; Tryptophan;Arginine or Glutamine
<220> FEATURE:
<221> NAME/KEY: Variant
<222> LOCATION: 19
<223> OTHER INFORMATION: Wherein Xaa can be Leucine or Arginine
<220> FEATURE:
<221> NAME/KEY: Variant
<222> LOCATION: 31
<223> OTHER INFORMATION: Wherein Xaa can be Glutamine or Aspartic Acid
<220> FEATURE:
<221> NAME/KEY: Variant
<222> LOCATION: 32
<223> OTHER INFORMATION: Wherein Xaa can be Asparagine; Aspartic Acid;
      Alanine;Glutamine;Tryptophan; Methionine or Serine
<220> FEATURE:
<221> NAME/KEY: Variant
<222> LOCATION: 33
<223> OTHER INFORMATION: Wherein Xaa can be Leucine; Isoleucine or
      Valine
<220> FEATURE:
<221> NAME/KEY: Variant
<222> LOCATION: 34
<223> OTHER INFORMATION: Wherein Xaa can be Tryptophan or Arginine
<220> FEATURE:
<221> NAME/KEY: Variant
<222> LOCATION: 35
<223> OTHER INFORMATION: Wherein Xaa can be Threonine or Phenylalanine
<220> FEATURE:
<221> NAME/KEY: Variant
<222> LOCATION: 37
<223> OTHER INFORMATION: Wherein Xaa can be Aspartic Acid; Tryptophan;
      Asparagine;
      Lysine; Serine; Glutamic Acid or Alanine
<220> FEATURE:
<221> NAME/KEY: Variant
<222> LOCATION: 38
<223> OTHER INFORMATION: Wherein Xaa can be Tryptophan or Glycine
<220> FEATURE:
<221> NAME/KEY: Variant
<222> LOCATION: 40
<223> OTHER INFORMATION: Wherein Xaa can be Glutamic Acid or Valine
<220> FEATURE:
<221> NAME/KEY: Variant
<222> LOCATION: 41
<223> OTHER INFORMATION: Wherein Xaa can be Alanine or Valine
<220> FEATURE:
<221> NAME/KEY: Variant
<222> LOCATION: 48
<223> OTHER INFORMATION: Wherein Xaa can be Glutamic Acid; Leucine
      or Arginine
```

```
<220> FEATURE:
<221> NAME/KEY: Variant
<222> LOCATION: 49
<223> OTHER INFORMATION: Wherein Xaa can be Threonine; Serine or
      Methionine
<220> FEATURE:
<221> NAME/KEY: Variant
<222> LOCATION: 51
<223> OTHER INFORMATION: Wherein Xaa can be Tyrosine or Serine

<400> SEQUENCE: 2

Gly Val Thr Leu Phe Val Ala Leu Tyr Asp Tyr Xaa Xaa Xaa Xaa Xaa
1               5                   10                  15

Xaa Asp Xaa Ser Phe His Lys Gly Glu Lys Phe Gln Ile Leu Xaa Xaa
            20                  25                  30

Xaa Xaa Xaa Gly Xaa Xaa Trp Xaa Xaa Arg Ser Leu Thr Thr Gly Xaa
        35                  40                  45

Xaa Gly Xaa Ile Pro Ser Asn Tyr Val Ala Pro Val Asp Ser Ile Gln
    50                  55                  60

<210> SEQ ID NO 3
<211> LENGTH: 63
<212> TYPE: PRT
<213> ORGANISM: Homo sapiens

<400> SEQUENCE: 3

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 4
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 4

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Gln Asp
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 5
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 5

Gly Val Thr Leu Phe Val Ala Leu Tyr Asp Tyr Gln Ser Arg His Gly
1               5                   10                  15
```

-continued

```
Phe Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

<210> SEQ ID NO 6
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 6

Gly Val Thr Leu Phe Val Ala Leu Tyr Asp Tyr Val Ser Asn Thr Gly
1               5                   10                  15

Phe Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

<210> SEQ ID NO 7
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 7

Gly Val Thr Leu Phe Val Ala Leu Tyr Asp Tyr Thr Ala Ser Tyr Gly
1               5                   10                  15

Tyr Asp Leu Ser Phe His Lys Gly Glu Lys Phe Gln Ile Leu Asp Asp
                20                  25                  30

Ile Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

<210> SEQ ID NO 8
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 8

Gly Val Thr Leu Phe Val Ala Leu Tyr Asp Tyr Leu Arg Arg Asn Ser
1               5                   10                  15

Pro Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

<210> SEQ ID NO 9
<211> LENGTH: 64
<212> TYPE: PRT
```

<213> ORGANISM: Artificial
<220> FEATURE:
<223> OTHER INFORMATION: derivative SH3 domain of the Fyn kinase

<400> SEQUENCE: 9

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Gln Asp
                20                  25                  30

Leu Trp Thr Gly Ala Leu Trp Arg Ala Arg Ser Leu Thr Thr Gly Arg
            35                  40                  45

Met Gly Ser Ile Pro Ser Asn Tyr Val Ala Pro Val Asp Ser Ile Gln
        50                  55                  60

<210> SEQ ID NO 10
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 10

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
                20                  25                  30

Leu Trp Thr Gly Glu Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 11
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 11

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
                20                  25                  30

Leu Trp Thr Gly Ser Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 12
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 12

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
                20                  25                  30

Leu Trp Thr Gly Lys Trp Trp Glu Ala Arg Ser Leu Thr Thr Gly Glu

```
                    35                  40                  45

Thr Gly Tyr Ile Pro Ser Asn Tyr Val Ala Pro Val Asp Ser Ile Gln
    50                  55                  60

<210> SEQ ID NO 13
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 13

Gly Val Thr Leu Phe Val Ala Leu Tyr Asp Tyr Glu Lys Gln His Ala
1               5                   10                  15

Trp Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 14
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 14

Gly Val Thr Leu Phe Val Ala Leu Tyr Asp Tyr Arg Ser Ser Tyr Glu
1               5                   10                  15

Trp Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 15
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 15

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Asn Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 16
<211> LENGTH: 64
<212> TYPE: PRT
<213> ORGANISM: Artificial
<220> FEATURE:
<223> OTHER INFORMATION: derivative SH3 domain of the Fyn kinase
```

-continued

```
<400> SEQUENCE: 16

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 17
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 17

Gly Val Thr Leu Phe Val Ala Leu Tyr Asp Tyr Gly Asn Phe Arg Trp
1               5                   10                  15

Arg Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 18
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 18

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Trp Gly Trp Val Ala Arg Ser Leu Thr Thr Gly Leu
        35                  40                  45

Ser Gly Tyr Ile Pro Ser Asn Tyr Val Ala Pro Val Asp Ser Ile Gln
    50                  55                  60

<210> SEQ ID NO 19
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 19

Gly Val Thr Leu Phe Val Ala Leu Tyr Asp Tyr Thr Ser Met Arg Gly
1               5                   10                  15

Tyr Asp Leu Ser Phe His Lys Gly Glu Lys Phe Gln Ile Leu Gln Asp
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 20
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 20

Gly Val Thr Leu Phe Val Ala Leu Tyr Asp Tyr Gln Ser Lys His Gly
1               5                   10                  15

Tyr Asp Leu Ser Phe His Lys Gly Glu Lys Phe Gln Ile Leu Gln Asp
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 21
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 21

Gly Val Thr Leu Phe Val Ala Leu Tyr Asp Tyr Leu Met Lys Thr Leu
1               5                   10                  15

Ala Asp Leu Ser Phe His Lys Gly Glu Lys Phe Gln Ile Leu Gln Asp
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 22
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 22

Gly Val Thr Leu Phe Val Ala Leu Tyr Asp Tyr Thr Leu Arg Gln Trp
1               5                   10                  15

Lys Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 23
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 23

Gly Val Thr Leu Phe Val Ala Leu Tyr Asp Tyr Glu Arg Gln His Gly
1               5                   10                  15

Phe Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 24
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 24

Gly Val Thr Leu Phe Val Ala Leu Tyr Asp Tyr Glu Ser Arg His Gly
1               5                   10                  15

Tyr Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 25
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 25

Gly Val Thr Leu Phe Val Ala Leu Tyr Asp Tyr Gln Ser Lys Gln Gly
1               5                   10                  15

Phe Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 26
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 26

Gly Val Thr Leu Phe Val Ala Leu Tyr Asp Tyr Leu Leu Gln Trp Arg
1               5                   10                  15

Gln Asp Leu Ser Phe His Lys Gly Glu Lys Phe Gln Ile Leu Gln Asp
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 27
<211> LENGTH: 64

```
<212> TYPE: PRT
<213> ORGANISM: Artificial
<220> FEATURE:
<223> OTHER INFORMATION: derivative SH3 domain of the Fyn kinase

<400> SEQUENCE: 27

Gly Val Thr Leu Phe Val Ala Leu Tyr Asp Tyr Thr Ser Ser His Gly
1               5                   10                  15

Phe Asp Leu Ser Phe His Lys Gly Glu Lys Phe Gln Ile Leu Gln Asp
                20                  25                  30

Leu Trp Thr Gly Asp Trp Trp Glu Val Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 28
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 28

Gly Val Thr Leu Phe Val Ala Leu Tyr Asp Tyr Glu Ala His Leu Gly
1               5                   10                  15

Tyr Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 29
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 29

Gly Val Thr Leu Phe Val Ala Leu Tyr Asp Tyr Thr Ala Val His Gly
1               5                   10                  15

Tyr Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 30
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 30

Gly Val Thr Leu Phe Val Ala Leu Tyr Asp Tyr Leu Thr Lys Gln Leu
1               5                   10                  15

Pro Asp Arg Ser Phe His Lys Gly Glu Lys Phe Gln Ile Leu Gln Asn
                20                  25                  30
```

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 31
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 31

Gly Val Thr Leu Phe Val Ala Leu Tyr Asp Tyr Met Ser Gln Met Gly
1               5                   10                  15

Tyr Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 32
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 32

Gly Val Thr Leu Phe Val Ala Leu Tyr Asp Tyr Gln Ala Ser His Gly
1               5                   10                  15

Tyr Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 33
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 33

Gly Val Thr Leu Phe Val Ala Leu Tyr Asp Tyr Thr Ala Arg Thr Gly
1               5                   10                  15

Tyr Asp Leu Ser Phe His Lys Gly Glu Lys Phe Gln Ile Leu Asp Ala
            20                  25                  30

Val Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 34
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 34

Gly Val Thr Leu Phe Val Ala Leu Tyr Asp Tyr Gln Ser Arg Glu Lys
1               5                   10                  15

Phe Asp Leu Ser Phe His Lys Gly Glu Lys Phe Gln Ile Leu Asp Gln
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 35
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 35

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Asp Asn
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 36
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 36

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Asp Asp
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 37
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 37

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Asp Trp
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln

<210> SEQ ID NO 38
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 38

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Asp Ala
            20                  25                  30

Ile Arg Phe Gly Asp Arg Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 39
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 39

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Asp Ala
            20                  25                  30

Met Leu Arg Phe Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

<210> SEQ ID NO 40
<211> LENGTH: 64
<212> TYPE: PRT
<213> ORGANISM: Artificial
<220> FEATURE:
<223> OTHER INFORMATION: derivative SH3 domain of the Fyn kinase

<400> SEQUENCE: 40

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Asp Ser
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 41
<211> LENGTH: 64
<212> TYPE: PRT
<213> ORGANISM: Artificial
<220> FEATURE:
<223> OTHER INFORMATION: derivative SH3 domain of the Fyn kinase
<220> FEATURE:
<221> NAME/KEY: Variant
<222> LOCATION: 12
<223> OTHER INFORMATION: Wherein Xaa can be Alanine; Valine; Isoleucine;

-continued

```
      Leucine; Methionine; Glycine; Proline; Serine;
      Threonine;Asparagine; Glutamine; Cysteine; Arginine;
      Histidine;Lysine; Aspartic Acid or Glutamic Acid
<220> FEATURE:
<221> NAME/KEY: Variant
<222> LOCATION: 13
<223> OTHER INFORMATION: Wherein Xaa can be Arginine; Histidine; Lysine;
      Alanine; Valine;Isoleucine; Leucine; Methionine; Glycine; Proline;
      Serine; Threonine; Asparagine; Glutamine or Cysteine
<220> FEATURE:
<221> NAME/KEY: Variant
<222> LOCATION: 14
<223> OTHER INFORMATION: Wherein Xaa can be Arginine; Histidine; Lysine;
      Serine; Threonine;Asparagine; Glutamine;Cysteine; Phenylalanine;
      Tyrosine; Tryptophan;Alanine; Valine; Isoleucine;
      Leucine;Methionine; Glycine or Proline
<220> FEATURE:
<221> NAME/KEY: Variant
<222> LOCATION: 15
<223> OTHER INFORMATION: Wherein Xaa can be Alanine; Cysteine;
      Phenylalanine; Glycine; Histidine; Isoleucine; Lysine; Leucine;
      Methionine;Asparagine;Proline; Glutamine; Arginine;
      Serine;Threonine;Valine;Tryptophan or Tyrosine
<220> FEATURE:
<221> NAME/KEY: Variant
<222> LOCATION: 16
<223> OTHER INFORMATION: Wherein Xaa can be any one of the naturally
      occurring amino acids
<220> FEATURE:
<221> NAME/KEY: Variant
<222> LOCATION: 17
<223> OTHER INFORMATION: Wherein Xaa can be Phenylalanine; Tyrosine;
      Tryptophan; Alanine; Valine;Isoleucine;Leucine; Methionine;
      Glycine; Proline; Arginine; Histidine;Lysine; Serine; Threonine;
      Asparagine; Glutamine or Cysteine
<220> FEATURE:
<221> NAME/KEY: Variant
<222> LOCATION: 19
<223> OTHER INFORMATION: Wherein Xaa can be Alanine; Valine; Isoleucine;
      Leucine; Methionine;Glycine; Proline; Arginine; Histidine or
      Lysine
<220> FEATURE:
<221> NAME/KEY: Variant
<222> LOCATION: 31
<223> OTHER INFORMATION: Wherein Xaa can be Serine; Threonine;
      Asparagine; Glutamine;Cysteine;Aspartic Acid or Glutamic Acid
<220> FEATURE:
<221> NAME/KEY: Variant
<222> LOCATION: 32
<223> OTHER INFORMATION: Wherein Xaa can be Serine; Threonine;
      Asparagine; Glutamine;Cysteine;Aspartic Acid or Glutamic Acid
<220> FEATURE:
<221> NAME/KEY: Variant
<222> LOCATION: 33
<223> OTHER INFORMATION: Wherein Xaa can be Alanine; Valine; Isoleucine;
      Leucine; Methionine;Glycine or Proline
<220> FEATURE:
<221> NAME/KEY: Variant
<222> LOCATION: 34
<223> OTHER INFORMATION: Wherein Xaa can be Phenylalanine; Tyrosine or
      Tryptophan
<220> FEATURE:
<221> NAME/KEY: Variant
<222> LOCATION: 35
<223> OTHER INFORMATION: Wherein Xaa can be Serine; Threonine;
      Asparagine; Glutamine or Cysteine
<220> FEATURE:
<221> NAME/KEY: Variant
<222> LOCATION: 37
<223> OTHER INFORMATION: Wherein Xaa can be any one of the naturally
      occurring amino acids
<220> FEATURE:
<221> NAME/KEY: Variant
<222> LOCATION: 38
<223> OTHER INFORMATION: Wherein Xaa can be Phenylalanine; Tyrosine;
      Tryptophan; Alanine; Valine; Isoleucine; Leucine; Methionine;
      Glycine or Proline
<220> FEATURE:
<221> NAME/KEY: Variant
```

```
<222> LOCATION: 40
<223> OTHER INFORMATION: Wherein Xaa can be Aspartic Acid; Glutamic
      Acid; Alanine; Valine; Isoleucine;Leucine;Methionine;
      Glycine or Proline
<220> FEATURE:
<221> NAME/KEY: Variant
<222> LOCATION: 41
<223> OTHER INFORMATION: Wherein Xaa can be Alanine; Valine; Isoleucine;
      Leucine;Methionine;Glycine or Proline
<220> FEATURE:
<221> NAME/KEY: Variant
<222> LOCATION: 48
<223> OTHER INFORMATION: Wherein Xaa can be Aspartic Acid; Glutamic
      Acid; Alanine; Valine; Isoleucine; Leucine; Methionine; Glycine;
      Proline;Arginine; Histidine or Lysine
<220> FEATURE:
<221> NAME/KEY: Variant
<222> LOCATION: 49
<223> OTHER INFORMATION: Wherein Xaa can be Serine; Threonine;
      Asparagine; Glutamine;Cysteine; Alanine; Valine;Isoleucine;
      Leucine; Methionine;Glycine or Proline
<220> FEATURE:
<221> NAME/KEY: Variant
<222> LOCATION: 51
<223> OTHER INFORMATION: Wherein Xaa can be Phenylalanine; Tyrosine;
      Tryptophan; Serine; Threonine;Asparagine; Glutamine or Cysteine

<400> SEQUENCE: 41

Gly Val Thr Leu Phe Val Ala Leu Tyr Asp Tyr Xaa Xaa Xaa Xaa Xaa
1               5                   10                  15

Xaa Asp Xaa Ser Phe His Lys Gly Glu Lys Phe Gln Ile Leu Xaa Xaa
            20                  25                  30

Xaa Xaa Xaa Gly Xaa Xaa Trp Xaa Xaa Arg Ser Leu Thr Thr Gly Xaa
        35                  40                  45

Xaa Gly Xaa Ile Pro Ser Asn Tyr Val Ala Pro Val Asp Ser Ile Gln
    50                  55                  60

<210> SEQ ID NO 42
<211> LENGTH: 64
<212> TYPE: PRT
<213> ORGANISM: Artificial
<220> FEATURE:
<223> OTHER INFORMATION: derivative SH3 domain of the Fyn kinase
<220> FEATURE:
<221> NAME/KEY: Variant
<222> LOCATION: 12
<223> OTHER INFORMATION: Wherein Xaa can be Valine; Threonine; Leucine;
      Histidine;Glutamine; Glutamic Acid; Arginine;
      Glycine or Methionine
<220> FEATURE:
<221> NAME/KEY: Variant
<222> LOCATION: 13
<223> OTHER INFORMATION: Wherein Xaa can be Serine; Alanine; Arginine;
      Lysine, Asparagine; Methionine; Leucine or Threonin
<220> FEATURE:
<221> NAME/KEY: Variant
<222> LOCATION: 14
<223> OTHER INFORMATION: Wherein Xaa can be Asparagine; Serine;
      Arginine; Histidine; Glutamine; Phenylalanine; Methionine;
      Lysine or Valine
<220> FEATURE:
<221> NAME/KEY: Variant
<222> LOCATION: 15
<223> OTHER INFORMATION: Wherein Xaa can be Threonine; Tyrosine;
      Asparagine; Leucine; Histidine; Arginine; Glutamine;Tryptophan
      or Methionine
<220> FEATURE:
<221> NAME/KEY: Variant
<222> LOCATION: 16
<223> OTHER INFORMATION: Wherein Xaa can be Glycine; Serine; Alanine;
      Glutamic Acid;Tryptophan; Leucine or Arginine
<220> FEATURE:
<221> NAME/KEY: Variant
<222> LOCATION: 17
```

<223> OTHER INFORMATION: Wherein Xaa can be Phenylalanine; Tyrosine;
    Proline; Tryptophan;Arginine or Glutamine
<220> FEATURE:
<221> NAME/KEY: Variant
<222> LOCATION: 19
<223> OTHER INFORMATION: Wherein Xaa can be Leucine or Arginine
<220> FEATURE:
<221> NAME/KEY: Variant
<222> LOCATION: 31
<223> OTHER INFORMATION: Wherein Xaa can be Glutamine or Aspartic Acid
<220> FEATURE:
<221> NAME/KEY: Variant
<222> LOCATION: 32
<223> OTHER INFORMATION: Wherein Xaa can be Asparagine or Aspartic Acid
<220> FEATURE:
<221> NAME/KEY: Variant
<222> LOCATION: 33
<223> OTHER INFORMATION: Wherein Xaa can be Leucine or Isoleucine
<220> FEATURE:
<221> NAME/KEY: Variant
<222> LOCATION: 37
<223> OTHER INFORMATION: Wherein Xaa can be Aspartic Acid; Tryptophan;
    Asparagine;Lysine; Serine;Glutamic Acid or Alanine
<220> FEATURE:
<221> NAME/KEY: Variant
<222> LOCATION: 38
<223> OTHER INFORMATION: Wherein Xaa can be Tryptophan or Glycine
<220> FEATURE:
<221> NAME/KEY: Variant
<222> LOCATION: 40
<223> OTHER INFORMATION: Wherein Xaa can be Glutamic Acid or Valine
<220> FEATURE:
<221> NAME/KEY: Variant
<222> LOCATION: 41
<223> OTHER INFORMATION: Wherein Xaa can be Alanine or Valine
<220> FEATURE:
<221> NAME/KEY: Variant
<222> LOCATION: 48
<223> OTHER INFORMATION: Wherein Xaa can be Glutamic Acid; Leucine or
    Arginine
<220> FEATURE:
<221> NAME/KEY: Variant
<222> LOCATION: 49
<223> OTHER INFORMATION: Wherein Xaa can be Threonine; Serine or
    Methionine
<220> FEATURE:
<221> NAME/KEY: Variant
<222> LOCATION: 51
<223> OTHER INFORMATION: Wherein Xaa can be Tyrosine or Serine

<400> SEQUENCE: 42

Gly Val Thr Leu Phe Val Ala Leu Tyr Asp Tyr Xaa Xaa Xaa Xaa Xaa
1               5                   10                  15

Xaa Asp Xaa Ser Phe His Lys Gly Glu Lys Phe Gln Ile Leu Xaa Xaa
                20                  25                  30

Xaa Trp Thr Gly Xaa Xaa Trp Xaa Xaa Arg Ser Leu Thr Thr Gly Xaa
            35                  40                  45

Xaa Gly Xaa Ile Pro Ser Asn Tyr Val Ala Pro Val Asp Ser Ile Gln
        50                  55                  60

<210> SEQ ID NO 43
<211> LENGTH: 5
<212> TYPE: PRT
<213> ORGANISM: Artificial
<220> FEATURE:
<223> OTHER INFORMATION: derivative src-loop of the SH3 domain of the
    Fyn kinase

<400> SEQUENCE: 43

Gln Asp Leu Trp Thr
1               5

-continued

```
<210> SEQ ID NO 44
<211> LENGTH: 5
<212> TYPE: PRT
<213> ORGANISM: Artificial
<220> FEATURE:
<223> OTHER INFORMATION: derivative src-loop of the SH3 domain of the
      Fyn kinase

<400> SEQUENCE: 44

Gln Asn Leu Trp Thr
1               5

<210> SEQ ID NO 45
<211> LENGTH: 5
<212> TYPE: PRT
<213> ORGANISM: Artificial
<220> FEATURE:
<223> OTHER INFORMATION: derivative src-loop of the SH3 domain of the
      Fyn kinase

<400> SEQUENCE: 45

Asp Asp Ile Trp Thr
1               5

<210> SEQ ID NO 46
<211> LENGTH: 609
<212> TYPE: PRT
<213> ORGANISM: Homo sapiens

<400> SEQUENCE: 46

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240
```

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
        595                 600                 605

Leu

<210> SEQ ID NO 47
<211> LENGTH: 608
<212> TYPE: PRT
<213> ORGANISM: Mus musculus

<400> SEQUENCE: 47

```
Met Lys Trp Val Thr Phe Leu Leu Leu Phe Val Ser Gly Ser Ala
1               5                   10                  15

Phe Ser Arg Gly Val Phe Arg Glu Ala His Lys Ser Glu Ile Ala
            20                  25                  30

His Arg Tyr Asn Asp Leu Gly Glu Gln His Phe Lys Gly Leu Val Leu
            35                  40                  45

Ile Ala Phe Ser Gln Tyr Leu Gln Lys Cys Ser Tyr Asp Glu His Ala
50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
            115                 120                 125

His Lys Asp Asp Asn Pro Ser Leu Pro Pro Phe Glu Arg Pro Glu Ala
            130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gln Arg Met Lys Cys
            210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
            245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
            275                 280                 285

Cys Glu Asn Gln Ala Thr Ile Ser Ser Lys Leu Gln Thr Cys Cys Asp
            290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
            325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
            370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
            405                 410                 415
```

Asp Leu Tyr Glu Lys Leu Gly Glu Tyr Gly Phe Gln Asn Ala Ile Leu
                420                 425                 430

Val Arg Tyr Thr Gln Lys Ala Pro Gln Val Ser Thr Pro Thr Leu Val
            435                 440                 445

Glu Ala Ala Arg Asn Leu Gly Arg Val Gly Thr Lys Cys Cys Thr Leu
450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
    530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

<210> SEQ ID NO 48
<211> LENGTH: 608
<212> TYPE: PRT
<213> ORGANISM: Rattus norvegicus

<400> SEQUENCE: 48

Met Lys Trp Val Thr Phe Leu Leu Leu Leu Phe Ile Ser Gly Ser Ala
1               5                   10                  15

Phe Ser Arg Gly Val Phe Arg Arg Glu Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Tyr Leu Gln Lys Cys Pro Tyr Glu Glu His Ile
    50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Phe Gln Arg Pro Glu Ala
    130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

```
Cys Thr Glu Ser Asp Lys Ala Ala Cys Leu Thr Pro Lys Leu Asp Ala
            195                 200                 205

Val Lys Glu Lys Ala Leu Val Ala Ala Val Arg Gln Arg Met Lys Cys
210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
                245                 250                 255

Lys Leu Ala Thr Asp Val Thr Lys Ile Asn Lys Glu Cys Cys His Gly
            260                 265                 270

Asp Leu Leu Glu Cys Ala Asp Asp Arg Ala Glu Leu Ala Lys Tyr Met
            275                 280                 285

Cys Glu Asn Gln Ala Thr Ile Ser Ser Lys Leu Gln Ala Cys Cys Asp
290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
370                 375                 380

Cys Ala Glu Gly Asp Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Glu Leu Tyr Glu Lys Leu Gly Glu Tyr Gly Phe Gln Asn Ala Val Leu
            420                 425                 430

Val Arg Tyr Thr Gln Lys Ala Pro Gln Val Ser Thr Pro Thr Leu Val
            435                 440                 445

Glu Ala Ala Arg Asn Leu Gly Arg Val Gly Thr Lys Cys Cys Thr Leu
450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
            515                 520                 525

Glu Thr Phe Thr Phe His Ser Asp Ile Cys Thr Leu Pro Asp Lys Glu
530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
            580                 585                 590

Ala Thr Glu Gly Pro Asn Leu Val Ala Arg Ser Lys Glu Ala Leu Ala
            595                 600                 605
```

```
<210> SEQ ID NO 49
<211> LENGTH: 64
<212> TYPE: PRT
<213> ORGANISM: Artificial
<220> FEATURE:
<223> OTHER INFORMATION: derivative SH3 domain of the Fyn kinase
<220> FEATURE:
<221> NAME/KEY: Variant
<222> LOCATION: 12
<223> OTHER INFORMATION: Wherein Xaa can be Threonine; Histidine or
      Glutamine
<220> FEATURE:
<221> NAME/KEY: Variant
<222> LOCATION: 13
<223> OTHER INFORMATION: Wherein Xaa can be Serine or Alanine
<220> FEATURE:
<221> NAME/KEY: Variant
<222> LOCATION: 14
<223> OTHER INFORMATION: Wherein Xaa can be Arginine or Histidine
<220> FEATURE:
<221> NAME/KEY: Variant
<222> LOCATION: 15
<223> OTHER INFORMATION: Wherein Xaa can be Threonine; Leucine;
      Histidine or Glutamic Acid
<220> FEATURE:
<221> NAME/KEY: Variant
<222> LOCATION: 16
<223> OTHER INFORMATION: Wherein Xaa can be Glycine or Lysine
<220> FEATURE:
<221> NAME/KEY: Variant
<222> LOCATION: 17
<223> OTHER INFORMATION: Wherein Xaa can be Phenylalanine or Tyrosine
<220> FEATURE:
<221> NAME/KEY: Variant
<222> LOCATION: 32
<223> OTHER INFORMATION: Wherein Xaa can be Asparagine; Aspartic Acid;
      Alanine; Glutamine; Tryptophan; Methionine or Serine
<220> FEATURE:
<221> NAME/KEY: Variant
<222> LOCATION: 33
<223> OTHER INFORMATION: Wherein Xaa can be Leucine or Isoleucine

<400> SEQUENCE: 49

Gly Val Thr Leu Phe Val Ala Leu Tyr Asp Tyr Xaa Xaa Xaa Xaa Xaa
1               5                   10                  15

Xaa Asp Leu Ser Phe His Lys Gly Glu Lys Phe Gln Ile Leu Asp Xaa
            20                  25                  30

Xaa Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 50
<211> LENGTH: 5
<212> TYPE: PRT
<213> ORGANISM: Artificial
<220> FEATURE:
<223> OTHER INFORMATION: peptide linker sequence

<400> SEQUENCE: 50

Gly Gly Gly Gly Ser
1               5

<210> SEQ ID NO 51
<211> LENGTH: 10
<212> TYPE: PRT
<213> ORGANISM: Artificial
<220> FEATURE:
<223> OTHER INFORMATION: peptide linker sequence

<400> SEQUENCE: 51
```

-continued

Gly Gly Gly Gly Ser Gly Gly Gly Ser
1               5               10

<210> SEQ ID NO 52
<211> LENGTH: 15
<212> TYPE: PRT
<213> ORGANISM: Artificial
<220> FEATURE:
<223> OTHER INFORMATION: peptide linker sequence

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 498
<212> TYPE: PRT
<213> ORGANISM: Artificial
<220> FEATURE:
<223> OTHER INFORMATION: bispecific T-cell engaging antibody

<400> SEQUENCE: 53

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Thr Tyr Arg Tyr Ser
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asn Ser Tyr Pro Tyr Thr Phe Gly Gly Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln

```
            275                 280                 285
Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 54
<211> LENGTH: 578
<212> TYPE: PRT
<213> ORGANISM: Artificial
<220> FEATURE:
<223> OTHER INFORMATION: bispecific T-cell engaging antibody fused to a
      derivative SH3 domain of the Fyn kinase

<400> SEQUENCE: 54

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
                20                  25                  30

Leu Trp Thr Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

Gly Gly Gly Gly Ser Gly Gly Gly Ser Gly Gly Gly Gly Ser
65                  70                  75                  80

Gln Val Gln Leu Val Glu Ser Gly Gly Leu Val Lys Pro Gly Glu
                85                  90                  95

Ser Leu Arg Leu Ser Cys Ala Ala Ser Gly Phe Thr Phe Ser Asp Tyr
                100                 105                 110

Tyr Met Tyr Trp Val Arg Gln Ala Pro Gly Lys Gly Leu Glu Trp Val
            115                 120                 125

Ala Ile Ile Ser Asp Gly Gly Tyr Tyr Thr Tyr Tyr Ser Asp Ile Ile
```

-continued

```
                130                 135                 140
Lys Gly Arg Phe Thr Ile Ser Arg Asp Asn Ala Lys Asn Ser Leu Tyr
145                 150                 155                 160

Leu Gln Met Asn Ser Leu Lys Ala Glu Asp Thr Ala Val Tyr Tyr Cys
                165                 170                 175

Ala Arg Gly Phe Pro Leu Leu Arg His Gly Ala Phe Asp Tyr Trp Gly
                180                 185                 190

Gln Gly Thr Leu Val Thr Val Ser Ser Gly Gly Gly Ser Gly Gly
                195                 200                 205

Gly Gly Ser Gly Gly Gly Ser Asp Ile Gln Met Thr Gln Ser Pro
210                 215                 220

Ser Ser Leu Ser Ala Ser Val Gly Asp Arg Val Thr Ile Thr Cys Arg
225                 230                 235                 240

Ala Ser Gln Asn Val Asp Thr Asn Val Ala Trp Tyr Gln Lys Pro
                245                 250                 255

Gly Gln Ala Pro Lys Ser Leu Ile Tyr Ser Ala Thr Tyr Arg Tyr Ser
                260                 265                 270

Asp Val Pro Ser Arg Phe Ser Gly Ser Ala Ser Gly Thr Asp Phe Thr
                275                 280                 285

Leu Thr Ile Ser Ser Val Gln Ser Glu Asp Phe Ala Thr Tyr Tyr Cys
                290                 295                 300

Gln Gln Tyr Asn Ser Tyr Pro Tyr Thr Phe Gly Gly Gly Thr Lys Leu
305                 310                 315                 320

Glu Ile Lys Ser Gly Gly Gly Gly Ser Glu Val Gln Leu Val Glu Ser
                325                 330                 335

Gly Gly Gly Leu Val Gln Pro Gly Gly Ser Leu Lys Leu Ser Cys Ala
                340                 345                 350

Ala Ser Gly Phe Thr Phe Asn Lys Tyr Ala Met Asn Trp Val Arg Gln
                355                 360                 365

Ala Pro Gly Lys Gly Leu Glu Trp Val Ala Arg Ile Arg Ser Lys Tyr
                370                 375                 380

Asn Asn Tyr Ala Thr Tyr Tyr Ala Asp Ser Val Lys Asp Arg Phe Thr
385                 390                 395                 400

Ile Ser Arg Asp Asp Ser Lys Asn Thr Ala Tyr Leu Gln Met Asn Asn
                405                 410                 415

Leu Lys Thr Glu Asp Thr Ala Val Tyr Tyr Cys Val Arg His Gly Asn
                420                 425                 430

Phe Gly Asn Ser Tyr Ile Ser Tyr Trp Ala Tyr Trp Gly Gln Gly Thr
                435                 440                 445

Leu Val Thr Val Ser Ser Gly Gly Gly Gly Ser Gly Gly Gly Gly Ser
                450                 455                 460

Gly Gly Gly Gly Ser Gln Thr Val Val Thr Gln Glu Pro Ser Leu Thr
465                 470                 475                 480

Val Ser Pro Gly Gly Thr Val Thr Leu Thr Cys Gly Ser Ser Thr Gly
                485                 490                 495

Ala Val Thr Ser Gly Asn Tyr Pro Asn Trp Val Gln Gln Lys Pro Gly
                500                 505                 510

Gln Ala Pro Arg Gly Leu Ile Gly Gly Thr Lys Phe Leu Ala Pro Gly
                515                 520                 525

Thr Pro Ala Arg Phe Ser Gly Ser Leu Leu Gly Gly Lys Ala Ala Leu
                530                 535                 540

Thr Leu Ser Gly Val Gln Pro Glu Asp Glu Ala Glu Tyr Tyr Cys Val
545                 550                 555                 560
```

-continued

```
Leu Trp Tyr Ser Asn Arg Trp Val Phe Gly Gly Gly Thr Lys Leu Thr
                565                 570                 575
Val Leu

<210> SEQ ID NO 55
<211> LENGTH: 27
<212> TYPE: PRT
<213> ORGANISM: Artificial
<220> FEATURE:
<223> OTHER INFORMATION: sequence of peptide derived from CD3

<400> SEQUENCE: 55

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25
```

UNITED STATES PATENT AND TRADEMARK OFFICE
CERTIFICATE OF CORRECTION

PATENT NO. : 9,790,475 B2
APPLICATION NO. : 14/758339
DATED : October 17, 2017
INVENTOR(S) : Fabian Buller et al.

It is certified that error appears in the above-identified patent and that said Letters Patent is hereby corrected as shown below:

In the Claims

Column 78, Line 30, Claim 7, after "The fusion protein of claim......" delete "5" and replace with -- 6 --.

Signed and Sealed this
Twenty-second Day of May, 2018

Andrei Iancu
*Director of the United States Patent and Trademark Office*